(12) United States Patent
Covarrubias Gallardo et al.

(10) Patent No.: US 11,134,687 B2
(45) Date of Patent: Oct. 5, 2021

(54) PREPARATION PROCESS OF DENTAL AND ORTHOPEDIC ACRYLIC MATERIALS WITH ANTIMICROBIAL PROPERTIES USING COPPER NANOPARTICLE TECHNOLOGY

(71) Applicant: Universidad de Chile, Santiago (CL)

(72) Inventors: Cristián Mauricio Covarrubias Gallardo, Santiago (CL); Sebastián Adolfo Correa Hernandez, Santiago (CL); Loreto Francisca Matamala Lopez, Santiago (CL); Juan Pablo Gonzalez Rojas, Rancagua (CL)

(73) Assignee: UNIVERSIDAD DE CHILE, Santiago (CL)

( * ) Notice: Subject to any disclaimer, the term of this patent is extended or adjusted under 35 U.S.C. 154(b) by 0 days.

(21) Appl. No.: 16/067,053

(22) PCT Filed: Dec. 29, 2016

(86) PCT No.: PCT/CL2016/050079
§ 371 (c)(1),
(2) Date: Jun. 28, 2018

(87) PCT Pub. No.: WO2017/113030
PCT Pub. Date: Jul. 6, 2017

(65) Prior Publication Data
US 2019/0021333 A1    Jan. 24, 2019

(30) Foreign Application Priority Data
Dec. 30, 2015    (CL) .................................. 3781-2015

(51) Int. Cl.
| | |
|---|---|
| *A01N 59/20* | (2006.01) |
| *A61K 33/34* | (2006.01) |
| *A61K 6/70* | (2020.01) |
| *A61K 6/887* | (2020.01) |
| *A01N 55/02* | (2006.01) |
| *A61K 47/32* | (2006.01) |

(52) U.S. Cl.
CPC ............. *A01N 59/20* (2013.01); *A01N 55/02* (2013.01); *A61K 6/70* (2020.01); *A61K 6/887* (2020.01); *A61K 33/34* (2013.01); *A61K 47/32* (2013.01)

(58) Field of Classification Search
CPC ................................ A01N 59/20; A61K 47/32
See application file for complete search history.

(56) References Cited

U.S. PATENT DOCUMENTS

| | | | |
|---|---|---|---|
| 6,679,937 B1 * | 1/2004 | Kodas .................. | C22C 1/1026 75/365 |
| 2014/0288171 A1 * | 9/2014 | Whang ................. | A01N 59/16 514/495 |

FOREIGN PATENT DOCUMENTS

| | | | |
|---|---|---|---|
| CL | 2014003518 A1 | 3/2015 | |
| WO | WO-2015006087 A1 | 1/2015 | |
| WO | WO-2016101082 A1 * | 6/2016 | ............. A61K 33/24 |

OTHER PUBLICATIONS

Sabatini, C. et al. "Incorporation of bactericidal poly-acrylic acid modified copper iodide particles into adhesive resins" J. Dentistry 2015, 43, 546-555 (Year: 2015).*

(Continued)

*Primary Examiner* — Andrew S Rosenthal
(74) *Attorney, Agent, or Firm* — Procopio, Cory, Hargreaves & Savitch LLP

(57) ABSTRACT

The present invention concerns a new biomaterial used to manufacture antimicrobial dental devices, intended to control the growth of microorganisms in the oral cavity. These include removable dentures (RD) with copper nanoparticles technology and antimicrobial properties against dental pathogens, such as: *Candida albicans*, a pathogen responsible for denture stomatitis; Pathogenic *Streptococcus mutans*, responsible for the initiation and progression of caries formation; and *Staphylococcus aureus*, which causes periprosthetic infections. This removable dental material allows for the production of a new dental device to prevent and/or control oral infections caused by said pathogens, such as denture stomatitis, secondary caries, periodontal diseases, among others.

7 Claims, 7 Drawing Sheets

(56) References Cited

OTHER PUBLICATIONS

King, S. et al. "Nanoparticle" Encyclopedia Britannica. May 14, 2019 (Year: 2019).*
Machine translation of WO2016/101082, pp. 1-8 (Year: 2016).*
Ma, X. et al. "Synthesis and Friction Properties of Copper/PMMA Composites by Soapless Emulsion Polymerization" Journal of Applied Polymer Science, vol. 122, 2837-2842 (2011) (Year: 2011).*
Beznis, N., et al., Cu-ZSM-5 Zeolites for the Formation of Methanol from Methane and Oxygen: Probing the Active Sites and Spectator Species, Catal Lett, 2010, 138:14-22.
Correa, S., Preparacion de Resinas Acrilicas Cargadas Con Nanoparticulas de Cobre y Sus Propiedades Antimicrobianas Frente a Candida Albicans, Instituto de Ciencias Odontologicas, Tesis Pregrado, Universidad de Chile: Santiago de Chile, [online 2012] (retreived from Internert Apr. 17, 2017) http://www.repositorio.uchile.cl/handle/2250/112937 see abstract.
Liu, et al., In Situ Synthesis of Hybrid Nancomposite with Highly Order Arranged Amorphous Metallic Copper Nanoparticle in Poli (2-hidroxyethyle Methacrylate) and Its Potential For Blood-Contact Uses, Acta Biomateralia, 2008, 4:2052-2058.
Palza, H., Antimicrobial Polymer Composites with Copper Micro- and Nanoparticles: Effect of Particle Size and Polymer Matrix Journal of Bioactive and Compatible Polymers, 2015, 1-15.
Palza, H., Antimicrobial Polymers With Metal Nanoparticles, Int. J. Mol. Sci., 2015, 16:2099-2116.
International Search Report issued in PCT/CL2016/050079 dated Apr. 26, 2017.

* cited by examiner

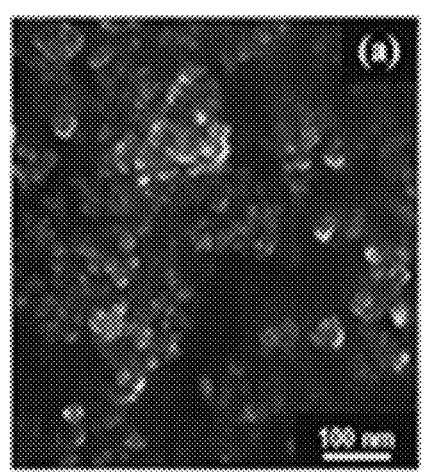 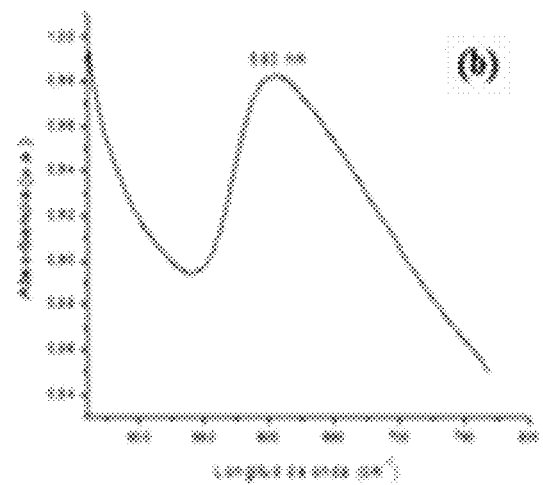
FIG. 3A　　　　　　　　　　FIG. 3B
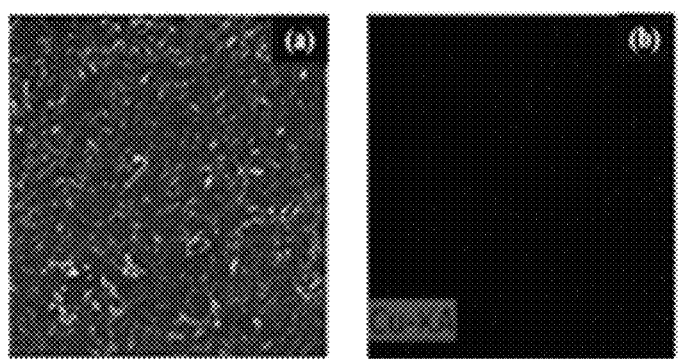 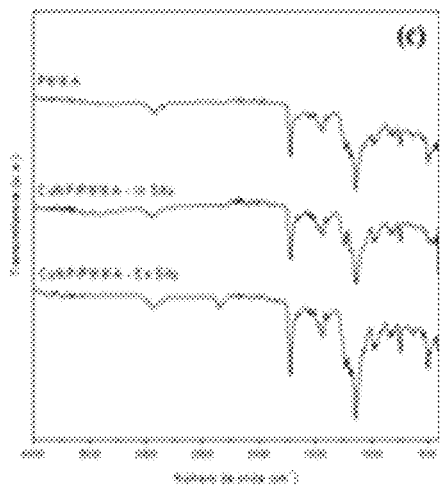
FIG. 4A　　　FIG. 4B　　　　　　FIG. 4C

PREPARATION PROCESS OF DENTAL AND ORTHOPEDIC ACRYLIC MATERIALS WITH ANTIMICROBIAL PROPERTIES USING COPPER NANOPARTICLE TECHNOLOGY

CROSS-REFERENCE TO RELATED APPLICATIONS

This application is the U.S. national stage of International Patent Application No. PCT/CL2016/050079, filed Dec. 29, 2016, which claims the benefit of Chilean Patent Application 3781-2015, filed Dec. 30, 2015.

OBJECT OF THE INVENTION

The object of the present invention consist in a production process for new acrylic biomaterial used to manufacture dental or medical products with antimicrobial properties, intended to control the growth of microorganisms in the oral cavity or in orthopedic treatments. These include, among others, removable and fixed dental prostheses, dental restoration resins, resin restoration adhesives, orthodontic bracket adhesives, cavity and orthopedic bone fissure sealants or cements based on copper nanoparticle technology and with antimicrobial properties against dental pathogens. These include particularly *Candida albicans*, the pathogen responsible for sub-prosthetic stomatitis; and *Streptococcus mutans*, the bacteria responsible for the formation of caries, as well as *Staphylococcus aureus*, which causes periprosthetic infections.

BACKGROUND OF THE INVENTION

The use of dental prostheses continues to be the most widely used dental rehabilitation solution, particularly in the lower socioeconomic strata. Prosthetic cleaning is essential to maintaining good oral hygiene and to prevent Subprosthetic Stomatitis, a chronic inflammation of the oral mucosa that is in contact with the prosthesis. Despite the fact that its etiology remains undefined, its main cause is linked to a fungal infection of the *Candida* genus. Since the vast majority prosthesis users are elderly seniors, cleaning habits are often poor, in part due to the visual and psychomotor limitations of this patient group. The current treatment for this type of infection is via oral and topical anti-fungal agents; however, these agents can lead to undesirable side effects for patients, such as general discomfort and a particularly unpleasant taste.

Our present aim is to develop therapeutic approaches based on the design of the prosthetic materials, obtaining antimicrobial nanocomposites. A nanocomposite is a material that combines various materials, such as polymers and metals, where one of them has nanometric dimensions. Copper is a well-known antimicrobial, displaying antibacterial and antifungal properties that are currently enhanced by the use of nanometrically-sized metal particles.

Removable prostheses are the most commonly used alternative in the rehabilitation of partially or totally edentulous patients, especially in groups with limited resources. They are also the main form of dental rehabilitation in primary care services due to their low cost. Being a foreign element, prostheses produce a biofilm on their surface, which cannot be removed by natural means. This biofilm can cause a chronic inflammation of the mucosa adjacent to the prosthesis, a condition known as Subprosthetic Stomatitis. This condition is characterized by inflammation and erythema of the mucosa covered by the prosthesis. It is asymptomatic and usually detected by clinical examination, since its less-observed symptoms such as a burning sensation occurs only in very few cases. Although its etiology has not yet been clearly defined, the infection of the mucosa is generally linked to *Candida albicans* and poor oral hygiene in patients (Gendreau, L. and Z. G. Loewy, *Epidemiology and Etiology of Denture Stomatitis*. Journal of Prosthodontics, 2011. 20(4): p. 251-260). Epidemiological studies show a prevalence of 15-70% with a higher incidence in older adults and women. It is generally estimated that two thirds of removable prosthesis users suffer from subprosthetic stomatitis to varying degrees.

*Candida albicans* is a yeast that normally occurs in the oral cavity, gastrointestinal tract and vagina, living commensally. Its pathogenicity is regulated by its virulence factors and the result of its interaction with the host immune response (Schaller M, Borelli C, Korting H C, Hube B. *Hydrolytic enzymes as virulence factors of Candida albicans*. Mycoses. 2005; 48(6):365-77). Virulence factors include transcription factors for cell membrane proteins, adhesins, proteolytic enzymes, and lipolytic enzymes (Calderone R A, Fonzi W A. *Virulence factors of Candida albicans*. Trends in Microbiology. 2001; 9(7):327-35), as well, has the ability to adhere to the cells and penetrate the epithelium (Machado A., Komiyama E., Santos S., Jorge A., Brighenti F., Koga-Ito C., *In vitro adherence of Candida albicans isolated from patients with chronic periodontitis*. J Appl Oral Sci. 2010; 384-387). In addition, *Candida albicans* occurs as a biofilm on the surface of the acrylic of dental prostheses, forming a closed matrix of yeast and hyphae microcolonies, containing a large number of bacteria, such as *Streptococcus* sps., extracellular polymers, and even a different phenotype from that found in planktonic state. This composition makes it much more resistant to antimicrobial agents (Douglas L J. *Candida biofilms and their role in infection*. Trends in Microbiology. 2003; 11(1): 30-6). In addition, *Candida albicans* is highly prevalent in the oral cavity, and it is commonly found in periodontal sacs, which may be somewhat related to the development or exacerbation of the clinical conditions related to periodontal disease (Urzúa B., Hermosilla G., Gamonal J., Morales-Bozo I., Canals M., Barahona S., et al. *Yeast diversity in the oral microbiota of subjects with periodontitis: Candida albicans and Candida dubliniensis colonize the periodontal pockets*. Med Mycol. 2008; 46:783-93; and Sardi J., Duke C., Mariano F., Peixoto I., Hofling J., Goncalves B. *Candida* spp. *in periodontal disease: a brief review*. J Oral Science. 2010. Vol. 52, No. 2, 177-185).

In patients with refractory periodontitis, 83.3% of the periodontal sacs present *Candida albicans*, hinting at a relationship between it and the way that periodontal microbiota is conformed (Machado et al). Canabarro et al., (Canabarro A., Valle C., Farias M R., Santos F B, Lazera M., Wanke B. *Association of subgingival colonization of Candida albicans and other yeast with severity of chrionic periodontitis*. J Periodont Res 2013; 48: 428-432) have hypothesized that deep structural epithelial disruption in the periodontal sac and immunosuppression caused by the severity of periodontal disease, would facilitate the colonization of subgingival *Candida albicans*. Therefore, there is clear evidence of the coexistence of *Candida albicans*, responsible for stomatitis and periodontal pathogens.

The first option treatment for subprosthetic stomatitis is the application of systemic and topical antifungals, such as Nystatin and Fluconazole. These antifungals can have undesirable side effects such as headaches, nausea, vomiting and general malaise, as well as generating discomfort and an unpleasant taste for the patient, which all but discourage following this type of treatment. Treatment with topical antifungals is known to be successful in eradicating *Candida albicans* infection and relieving its symptoms, but if the prosthesis is not properly and hygienically maintained, subprosthetic stomatitis will recur once the treatment is over (Gendreau et al).

In the search for new therapeutic alternatives, it has been observed that modifying the surface characteristics of the acrylic material is an effective method to reduce the adhesion of *Candida albicans* to the prosthesis (Park, S. E., et al., *Candida albicans Adherence to Surface-Modified Denture Resin Surfaces. Journal of Prosthodontics*, 2008. 17(5): p. 365-369). By modifying the chemical and physical properties of medical materials, they can be given antimicrobial properties to prevent and control infections. Studies have been conducted to incorporate antifungal compounds into the acrylic of the prosthesis, such as modifying its surface by impregnating it with histamines and salivary defensins (Pusateri C R, Monaco E A, Edgerton M. *Sensitivity of Candida albicans biofilm cells grown on denture acrylic to antifungal proteins and chlorhexidine*. Archives of Oral Biology. 2009; 54(6):588-94). Redding et al. prepared a polymeric coating loaded with chlorhexidine, nystatin and amphotericin, with the chlorhexidine coating exhibiting the best results (Redding S, Bhatt B, Rawls H R, Siegel G, Scott K, Lopez-Ribot J. *Inhibition of Candida albicans biofilm formation on denture material*. Oral Surgery, Oral Medicine, Oral Pathology, Oral Radiology, and Endodontology. 2009; 107(5):669-72).

For centuries metals have been known to possess antimicrobial properties and they are currently being studied for use in many applications with the help of nanotechnology, such as surface disinfection and topical application in gels and pastes. Copper, which has been widely used in medicine since the 19th century, was indicated in the treatment of skin infections, lupus, and was even used as an antimicrobial agent until the appearance of antibiotics in 1932 (Grass, G., C. Rensing, and M. Solioz, *Metallic Copper as an Antimicrobial Surface*. Applied and Environmental Microbiology, 2011. 77(5): p. 1541-1547). Copper has been used for decades for its antifungal properties (Cioffi, N., Torsi, L., Ditarantano, N., Tantalillo, G., Ghibelli, L., Sabbatini, L., Bleve-Zacheo, T., D'Alessio, M., Zambonin, P G., Traversa, E., *Copper nanoparticle/polymer composites with antifungal and bacteriostatic properties*. Chem. Mater, 2005, 17, 5255-5262; and Palza, H., Quijada, R., Delgado, K., *Antimicrobial polymer composites with copper micro- and nanoparticles: Effect of particle size and polymer matrix. Journal of Bioactive and compatible polymers*. 2015, 1-15).

Nevertheless, in recent years there has been a resurgence of interest in the use of the antimicrobial properties of this metal, mainly due to the possibility of producing nanometrically-sized copper particles.

The manipulation of the structure and application of nanometrically-sized materials is known as nanotechnology, which is based on controlling the properties of materials at a nanometric scale (1-100 nm) with the purpose of exploiting the different characteristics of nanodimensional materials (Ravishankar Rai V. and Jamuna Bai A., *Nanoparticles and their potential application as antimicrobials. Science against microbial pathogens: communicating current research and technological advances* 2011. 1(1): p. 10). The development of nanotechnology is expected to bring about important advances in the biological and biomedical sciences by providing the tools to understand the structures of materials and tissues, as well as to design technologies for their exploration, treatment, and even reconstruction (Ahmed, W., A. Elhissi, and K. Subramani, Chapter 1—*Introduction to Nanotechnology, in Nanobiomaterials in Clinical Dentistry*, K.S.A.K. Hartsfield, Publisher. 2013, William Andrew Publishing. p. 3-16). Due to their size, nanoparticles acquire new properties to those observed in micrometric structures. These properties are determined by the effect generated by the atoms located in the superficial layer of the structure and by the fact that they have a greater surface area in relation to the volume of the nanoparticles, in comparison to that of the micro or macrometric structures (Ren, G., et al., *Characterisation of copper oxide nanoparticles for antimicrobial applications. International Journal of Antimicrobial Agents*, 2009. 33(6): p. 587-590). One of the most studied metal nanoparticles is Silver (AgNP), which has proven antibacterial properties against *Escherichia coli, Staphylococcus aureus*, and *Klebsiella pneunomiae* (Ravishankar et al).

With respect to copper (CuNP), better antimicrobial properties have been observed in its nanoparticle form when compared to micro size (Theivasanthi, T., *Studies of Copper Nanoparticles Effects on Micro-organisms. Annals of Biological Research*, 2011. 2(3): p. 368-373). It has also been an effective killer of numerous strains of hospital-acquired infections, although there is a need for controlled release of ions into the local environment to achieve optimal antimicrobial activity (Ren, G., et al.). The antimicrobial properties of CuNPs have so far been assessed against the bacteria *Escherichia coli, Staphylococcus aureus, Klebsiella pneunomiae, Lysteria monocytogenes* and *Pseudomonas aeruginosa*; as well as against *Saccharomyces cerevisiae* yeast. However, the prior art shows no evidence regarding its effect on oral bacteria.

Research on the bactericidal mechanism of copper as a nanoparticle shows that the effect is largely due to its small size and large contact surface, in relation to its volume, which allows for easy interaction with microbial membranes. (Chatterjee A K, Ruchira C, Tarakdas B. *Mechanism of antibacterial activity of copper nanoparticles*. Nanotechnology. 2014; 25(13):135101).

A widely accepted method of action is cell death by contact, which occurs after a succession of events: damage to the cell membrane, entry of copper into the cell, formation of reactive species of oxygen by copper ions involved in the redox reaction and subsequent degradation of DNA, leading to cell death (Grass et al.). In a 2014 study, new information was reported about the antibacterial mechanism of action of copper nanoparticles. In the CuNP study on *Escherichia coli*, a change in bacterial morphology towards filamentous formation and subsequent cell death was observed. This effect is attributed to the cellular response caused by an overproduction of reactive oxygen species, resulting in considerable lipid peroxidation, protein oxidation and protein degradation. DNA (Chatterjee et al.). However, the authors also conclude that there is probably no single mechanism of bactericidal action for CuNP, the active agent being either the nanoparticle itself or the metal ions released from the particle. The latest evidence indicates that the greatest antimicrobial effect would be produced by the release of ions from nanoparticles (Palza, H., *Antimicrobial Polymers with Metal Nanoparticles*. Int. J. Mol. Sci. 2015, 16, 2099-2116).

While there have been no studies about the effects of copper nanoparticles on *Candida albicans*, there are studies regarding topical use of AgNP on *Candida albicans* biofilms formed on acrylic surfaces that report biocidal effects for both strains (Monteiro, D. R., et al., *Silver colloidal nan-* oparticle stability: influence on Candida biofilms formed on denture acrylic. Medical Mycology, 2014. 52(6): p. 627-635); y Candida glabrata (Silva, S., et al., The effect of silver nanoparticles and nystatin on mixed biofilms of Candida glabrata and Candida albicans on acrylic. Medical Mycology, 2013. 51(2): p. 178-184).

The antimicrobial capacity of these particles has led to exploring the possibility of modifying the acrylic material of the prostheses, incorporating metallic nanoparticles into their polymer matrix. Kamikawa et al. examined the adhesion of Candida albicans and Candida glabrata to dental acrylics modified with a polymeric coating loaded with AgNP, noting a considerable reduction in the growth of Candida albicans colonies (Kamikawa, Y., et al., In Vitro Antifungal Activity against Oral Candida Species Using a Denture Base Coated with Silver Nanoparticles. Journal of Nanomaterials, 2014. 2014: p. 6). Other approaches have tested incorporating AgNP inside the acrylic resin. These materials are known for their ability to release the active agent in a controlled manner and thus control the growth of microorganisms on the surface of the prosthesis. The existence of a dental prosthesis with these antimicrobial characteristics would allow for the prevention and treatment of stomatitis, unlike antifungal therapy, which only treats the disease. Using this strategy of modifying the acrylic material, (Nam K-Y, Lee C-H, Lee C-J. Antifungal and physical characteristics of modified denture base acrylic incorporated with silver nanoparticles. Gerodontology. 2012; 29(2): e413-e9), AgNP was added to acrylic prostheses by mixing colloidal silver suspensions with acrylic, using silver contents between 20-30% by weight, achieving a significant inhibition of Candida albicans with respect to the control group. A sustained release of silver over time was also observed, which maintained antifungal properties. However, the dark color of the resulting nanocomposite material produced by the AgNP particles is a clear disadvantage from a dental-aesthetic point of view.

On the other hand, CuNPs have been used to prepare various polymeric nanocomposites with antimicrobial properties. Polymers such as CuNP-charged polyvinyl ketone have also been studied, exhibiting the capacity to slowly release metal in a controlled manner, as well as to inhibit the growth of bacteria and fungi such as Saccharomyces cervisiae; and antimicrobial activity directly correlates with the concentration of nanoparticles (Cioffi et al.). Other polymers that have been studied are plant and bacterial cellulose matrices charged with nanostructures, such as nanofilaments and CuNP, exhibiting bactericidal action against Staphylococcus aureus and Klebsiella pneunomiae. This polymer has a potential application for use in wrapping papers (Theivasanthi et al.). With respect to CuNP-modified acrylic polymers, Liu et al. (Liu, Y Y., Liu, D M., Chen, S Y., Tung T H., Liu T Y., In situ synthesis of hybrid nanocomposite with highly order arranged amoorphous metallic copper nanoparticle in poli (2-hidroxyethyl methacrylate) and its potential for blood-contact uses. Acta Biomaterialia, 2008, (4), 2052-2058), incorporated CuNP into a poly(2-hydroxyethyl methacrylate (pHEMA) matrix used to manufacture biomedical devices with cardiovascular application. The results show that the addition of CuNP (0.03-0.15% copper) reduces platelet adhesion, thus avoiding the production of blood thrombi; however, no antimicrobial properties of the nanocomposite material were examined in this study. With respect to the antimicrobial mechanism of polymeric/metallic nanocomposites, an ion release mechanism is proposed, produced by the corrosion of the nanoparticles present in the matrix due to the diffusion of water molecules from the external environment. The diffusion of water molecules has been observed even in non-polar polymer matrices, such as polyethylene and polypropylene (Palza et al., y Ton-That, T M., Jungnickel, B J. Water diffusion into transcrystalline layers on polypropylene. J. Appl. Polum. Sci. 1999, 74, 3275-3285). Corrosion of the polymer can also happen over time, leading to the release of ions and contributing to the sustained release of copper over time (Palza et al.).

The addition of metal nanoparticles to dental acrylics to provide them with antimicrobial properties supposes certain advantages over traditional organic antimicrobials. Antibiotics generate microbial resistance and systemic negative side effects in patients, so the prior art suggests investigating new antibacterial alternatives (Nam et al.). On the other hand, in one study chlorhexidine was incorporated to dental acrylics, finding that this type of compounds undergoes a rapid release in an aqueous medium. A high release of residual monomer due to an incomplete polymerization was also found (Wilson, S J1, Wilson, H J. The release of chlorhexidine from modified dental acrylic resin J Oral Rehabil. 1993 May; 20(3):311-9). Furthermore, dental agents such as chlorhexidine have been studied in methylcellulose and polyacrylic acid gels, with a release temperature between 22 and 42° C. (Musial, W., Kokol, V., Voncina, B., Deposition and release of chlorhexidine from non-ionic and anionic polymer matrices. Chemical Papers, 2010 (64), 3, 346-353). In general, the addition of organic antimicrobials presents a high rate of release with increasing temperature, which can be expected to result in a high loss of the active agent when used under the thermopolymerization conditions of the prosthesis acrylic (temperatures above 90° C., under pressure). These aspects of stability of the antimicrobial agent under thermal curing conditions could be improved by using metal nanoparticles, such as copper.

It is a well-known fact that the oral cavity is a habitat for a set of microorganisms (microbial community). In here, the development of tooth decay is mediated by complex mechanisms that are initiated by a variety of factors, including genetic, behavioral, environmental and microbial factors. In the case of microbial factors, the presence of pathogens is essential for the onset and progression of caries damage; without bacteria there is no damage. In fact, it is a polymicrobial infectious disease, in which each individual bacterial species can collectively contribute to the total cariogenicity of the dental plaque bio-community (dental biofilm) associated with caries. The intrinsic sources of nutrients for microorganisms in the oral cavity are the materials found around the teeth: exudates, degraded epithelial cells and saliva components. Certain salivary proteins provide amino acids that influence the growth of Streptococcus mutans and Streptococcus sanguis. The saliva of subjects with caries better influences the growth of Streptococcus mutans. In addition, the food we eat remains in the oral cavity and serves as an extrinsic source of nutrients for the oral microflora.

Dental caries is an infectious disease originated by several factors. Microorganisms organized in a biofilm, called dental plaque, are essential in the development of caries lesions, which occur in the late stages of the disease. At each stage of lesion progression, microbial species predominate as a result of a succession of microorganisms. In the case of healthy caries-free subjects, the prevalence of microorganisms other than those associated with the disease has been observed, such as Streptococcus sanguinis. However, in subjects affected by dental caries, streptococci belonging to the mutans group have been the most prevalent during the onset and progression of the lesion, especially Streptococcus

*mutans*, while *Lactobacillus* and *Bifidobacterium* are predominant in the advanced stages of the lesion.

Another type of microbial disease that affects oral tissues is related to the microorganism *Candida albicans*, which is a type of yeast that causes subprosthetic stomatitis from the use of a dental prosthesis. This microorganism generally develops due to a poor fit or poor cleaning of the prosthesis. Subprosthetic stomatitis related to *C. albicans* is a non-specific inflammatory reaction to antigens, toxins and microbial enzymes produced by colonizing microorganisms, which is a serious infection of the oral mucosa. It is a common and periodic disease affecting up to 67% of dental prosthesis users. Factors such as poor oral hygiene, high carbohydrate intake, reduced salivary flow, continued use of the prosthesis, aging, malnutrition, immune suppression, radiation therapy, diabetes mellitus, and possibly antibiotic treatment are known to increase susceptibility to *C. albicans*.

Biomaterials can be of artificial or biological origin. The former can be made of metal, polymeric and ceramic materials. Metal implants, along with their alloys, are the most commonly used for orthopedic implants (nails, wires, plates) and dental implants (screws), as they must have a high resistance to mechanical wear and be able to support the proper load for their function. The metals used to manufacture these implants are: stainless steel, cobalt alloys with chromium, molybdenum and nickel, pure titanium (Ti) and its alloys with aluminum and vanadium. Examples of biological biomaterials include bone fragments, skin grafts, extracellular matrices and stem cells (human or animal).

Today, with the advent of nanotechnology, certain nanomaterials have been developed, particularly inorganic nanoparticles (NPs), which have a marked microbicidal effect on a wide variety of microorganisms, such as viruses, bacteria and fungi. The microbicidal capacity of NPs is linked to the nature of the material and to their intrinsic characteristics, such as their nanometric sizes (which allows for easier assimilation into microorganisms) and the high area/volume ratio that allows for greater contact and interaction with these microorganisms. Among the metallic NPs that have been shown to have microbicidal properties, the most important are silver, zinc oxide, copper or iron oxides. The first three substances already exhibit this property in their macroscopic form, while iron oxides are only microbicidal in nanostructured form. NPs have completely different mechanisms of microbicidal action from traditional antibiotics, providing a promising alternative. The mechanisms of bactericidal action of metallic NPs have not been fully elucidated, although several types of mechanisms have been proposed. These include disturbances in the functions of the cell membrane (which alter permeability and cell respiration), the entry of nanoparticles into the cell, which causes an alteration in the functions of proteins and DNA, or the production of oxidative species due to the presence of NPs inside the cell. It is not easy to make a comparative analysis of the data in the literature as the bactericidal action will depend on a wide variety of factors including: the size and shape of the NPs, their chemical composition, the coating and their potential surface charge and the concentration of NPs used.

The preparation of this dental material is achieved by incorporating copper nanoparticles (CuNPs) into the material through its in-situ formation from a copper precursor or by direct addition after synthesis. The advantage of this technology lies in the fact that it does not alter the commercial process currently used for the production of prostheses, since it is based on the same resin that is currently used without altering it. It is hoped that these new prosthetic devices with copper nanoparticle technology will present antifungal properties to prevent and/or treat subprosthetic stomatitis and to reduce the amount of cariogenic bacteria in users with dental prostheses. In short, the technology proposed to develop antimicrobial prosthesis material considers the synthesis and/or incorporation of the CuNPs during the preparation process of the prostheses that are currently sold, which would facilitate the market penetration of our methodology.

Various efforts have been made to provide antimicrobial action to dental devices and materials, including the following:

Document RU 2444349 describes a modified adhesive composition for attaching prostheses, which contains a percentage by weight of: polyvinylpyrrolidone-5, polyacrylic acid-15, glycerol-4, antiseptic cetrimide; sodium alginate-5, balsamic fir-10, silver nanoparticles of 1 to 5 nm size, and the rest is distilled water. The simplicity, safety and efficacy of the modified adhesive composition developed for denture attachment allows it to be used in common orthopedic practice, where the adhesive composition provides a considerable reduction in the adaptation period for edentulous patients with total denture prostheses. It does not cause any toxic side effects on the area tissues or the supporting body of the prosthesis as a whole, and exhibits optimal adhesive properties, remaining intact for a long time after eating hot food.

Document US 2013014671 describes an antimicrobial dental material that is characterized by the addition of approximately 0.1 to 0.5% of antibacterial metal particles by weight to a zirconium oxide (ZrO2) as a powder substrate of antimicrobial dental material. The metallic material has excellent ion-releasing antibacterial properties, which include silver, gold, platinum, palladium, iridium, titanium, copper, tin, antimony, bismuth and zinc, with a special preference for silver, copper and titanium. After being completely mixed and sintered from the antibacterial metal particles, it diffuses naturally into the zirconium oxide substrate, resulting in an antimicrobial dental material for dental implants or prostheses, or any other kind of oral reconstruction.

Document U.S. Pat. No. 6,267,590 describes a dental appliance, such as an orthodontic appliance, that is placed in the mouth and has an inorganic antimicrobial agent on a surface, and whose agent is preferably zeolite. The dental appliance may contain metal or a polymer (polycarbonate) and the agent may be present in a coating that is applied to the surfaces of the appliance to be contacted by liquids or solids in the mouth. The appliance may consist of a polymer resin or an elastomer incorporating the agent. A preferred antimicrobial agent is ceramic particles (e.g. zeolite particles) containing antimicrobial metal ions, e.g. silver ions, as the active agent.

Document U.S. Pat. No. 3,476,854 describes a formulation of an acrylic material (alkyl methacrylates), silicone resins, vinyl copolymers, and polyamide to form denture liners or tissue conditioners, loaded with antifungal compounds of zinc carboxylates (undecylenate). Said antifungal agent is dispersed in the resin and selected from heavy metal salts of monocarboxylic fatty acids, to medium chain length fatty acids, benzoic acid, benzyl benzoate, benzyl benzoic acid, salicylic acid, and benzyl salicylate. The resin contains enough antifungal agent to delay the growth of fungi, with said agent comprising at least 1% of its weight.

Document EP 2536379 A2 describes an antibacterial dental prosthesis comprising a polymeric substrate with a functional polymeric component and a slow-release antifungal agent. Said agent is bonded to the functional polymeric component so that it is slowly eluted from the functional polymeric component over a prolonged period of time.

Document EP 0081962 A2 describes a compressed solid composition used to clean dental prostheses, which is highly effervescent when added to water. It consists of a mixture of perborate, dichloroisocyanurate and an alkali, which produces a pH 11 cleaning solution.

Document EP 0400080 B1 describes a method of providing a dental prosthesis with a protective coating, which includes applying an aqueous dispersion of a non-toxic, antibacterial polysaccharide coating to the prosthesis. This reduces the adhesion of *Streptococcus salivarius* cells on acrylic resin prostheses by at least 25% compared to an uncoated control.

Document EP 1003791 A4 describes a formulation of an antimicrobial adhesive cleansing cream for dental prostheses, comprising nystatin or a combination of 8-hydroxyquinoline (or its salt) and at least one copper (II) salt, where the formulation is intended to prevent prosthetic stomatitis by inhibiting *Candida albicans*.

Document U.S. Pat. No. 4,332,791 describes an aqueous composition for toothpaste containing at least one water-soluble copper compound and at least one polishing agent, most of which is silicon dioxide.

Document EP 0471396 describes an oral composition comprising a bicarbonate salt, a copper compound present in an effective amount to inhibit bacterial growth and a complexing agent present in an effective amount to stabilize the copper compound.

Document US 2011/0229534 A1, describes oral care formulations comprising an anti-irritant amount of a salicylate salt and an effective amount of a flavor enhancer, in addition to an anti-inflammatory amount of an irritant agent, e.g. ketorolac. These oral care formulations can be used in a variety of devices to treat and/or prevent mucosal irritation such as ulcers.

Document U.S. Pat. No. 9,034,354 B2 describes antibacterial and antimicrobial surface coatings and dental materials using the antimicrobial properties of copper calcogenide and/or copper halide (CuQ, where Q=calcogen including oxygen, or halogen, or nothing). An antimicrobial barrier is created by adding adequately sized CuQ nanoparticles at a necessary and sufficient concentration in order to create a unique bioelectric environment. The biocidal efficacy of this unique bioelectric environment is achieved through a multi-factorial mechanism comprising a combination of the intrinsic quantum flux of copper ions (Cu0, Cu1+, Cu2+) and the high surface-to-volume electron sink facilitated by the nanoparticles. The result is a quantum constant flow of copper that manifests itself and establishes the antimicrobial environment to prevent or inhibit bacterial growth. The presence of CuQ results in inhibition or delay of bacterial destruction and endogenous enzymatic decomposition of the interdiffusion resin zone, whose integrity is essential for the longevity of dental restoration. Thus, this invention is designed for a bacteriostatic/bactericidal and anti-collagenolytic adhesive used to control the invasion and proliferation of microorganisms.

With regard to the use of copper for the control of subcutaneous stomatitis, document EP 1003791 A4 describes a formulation of an antimicrobial adhesive cream for dental prostheses, in which the active ingredient of the adhesive consists of 8-hydroxyquinoline (0.0001-0.5%) and a copper salt II (0.001-0.3%), which has produced greater activity against *C. albicans* in in-vitro tests.

Copper is also an active agent in toothpaste formulations with microbial plaque control properties. Thus, document U.S. Pat. No. 4,332,791 describes a toothpaste containing silica and copper salt (0.001-5%) as active components, whereas in document EP 0471396 A1, the active ingredient consists of a copper salt (0.01-5%), sodium bicarbonate and an alkylamine that acts as a stabilizer of the metal ion. Salts such as copper salicylate (0.05-0.3%) have also been used in the formulation of mouthwashes for the control of oral ulcers and irritations, as described in document US 2011/0229534 A1.

Most of the dental materials currently used to prepare restorations, implants, orthodontic elements, prostheses and others lack antimicrobial properties to control microbial activity in the oral cavity. Therefore, the prior art does not describe the preparation of acrylic-based dental prostheses (PMMA) with copper, using this element as an antimicrobial additive, either in salt or nanoparticle form.

Copper nanoparticles were not found in any formulations of dental products or materials, or in oral health therapies either.

BRIEF DESCRIPTION OF DRAWINGS

FIG. 3A illustrates a SEM microscopic image of copper nanoparticles (CuNP) synthesized in-situ in a acrylic monomer.

FIG. 3B illustrates a SEM image of copper nanoparticles synthesized by an in-situ method in acrylic monomer.

FIGS. 4A, 4B and 4C illustrate the presence of copper nanoparticles in a nanocomposite acrylic matrix.

DETAILED DESCRIPTION OF THE INVENTION

Figure 1:
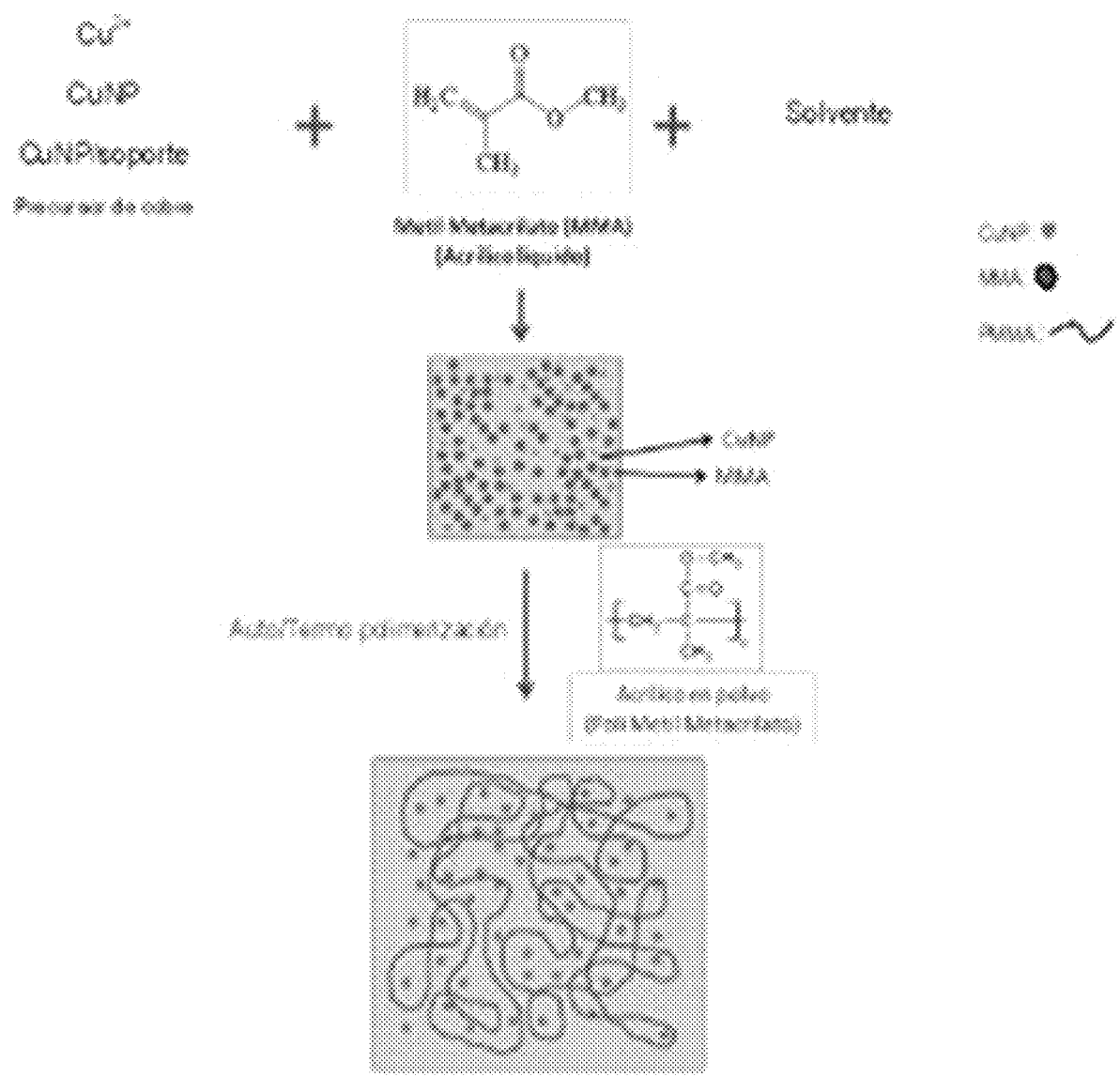
FIG. 1 illustrates a preparation process of the nanocomposite.

The present invention focuses on the development of a new material to manufacture a dental prosthesis device with antimicrobial properties, preferably to prevent subprosthetic stomatitis caused by the pathogen *Candida albicans*, and the reduction of bacteria such as *Streptococcus mutans*, a pathogen responsible for the initiation and progression of caries formation. In addition, the synthesis of the antimicrobial material for prostheses using copper nanoparticles as an antifungal agent is described preferably through the addition of copper nanoparticles inside a thermocuring acrylic resin, resulting in a prosthetic material with antimicrobial properties, especially against *Candida albicans* and particularly against *Streptococcus mutans*, and that retains its mechanical, color and cytocompatibility properties.

A preferred embodiment of the present invention consists of an antimicrobial nanocomposite CuNP/PMMA dental prosthesis material based on copper nanoparticles (CuNP) and polymethylmethacrylate (PMMA), comprising the CuNP dispersed in this resin and formed on-site during the thermopolymerization (heat-curing) process from a copper salt as a precursor.

Another preferred embodiment of the present invention consists of a nanocomposite material that includes CuNP/PMMA heat-curing based on copper nanoparticles (CuNP) and polymethylmethacrylate (PMMA); whereby the applications of said nanocomposite material (acrylic polymers with CuNP) are performed in: removable or fixed dental prostheses; dental restoration resins; resin adhesives (adhesive to bond the restorative resin to the tooth), pit and fissure sealants (acrylic sealant used to prevent the development of caries from minor fissures in the teeth, widely used in children), or orthodontic adhesives (used to adhere the bracket to the tooth surface), glass ionomer (a versatile material in dentistry, which can be used as a restoration, temporary in adults or permanent in children, or as a cementing agent for other dental materials) and bone or surgical cement (self-healing acrylic used to attach orthopedic prostheses to bone or in cranioplasties).

Another preferred embodiment of the present invention consists of an antimicrobial dental sealant comprising a dental sealant; and an antimicrobial dental resin with an antimicrobial amount of copper nanoparticles (CuNP).

Another preferred embodiment of the present invention provides a method to prevent secondary dental caries, including the application of a nanocomposite restoration dental resin based on copper nanoparticles (CuNP).

Another preferred embodiment of the present invention provides a method to prevent or inhibit dental caries by applying an antimicrobial dental sealant to tooth pits and fissures, whereby said antimicrobial sealant includes an antimicrobial dental resin with an antimicrobial amount of copper nanoparticles (CuNP).

Another preferred embodiment of the present invention provides a method to inhibit or limit microbial growth in the area of the enamel that is in contact with orthodontic brackets, through the use of an antimicrobial orthodontic adhesive with copper nanoparticles (CuNP).

It should be noted that in each of the preferred embodiments, copper nanoparticles (CuNP) have a copper particle size of between 40 and 100 nm.

The existence of a dental prosthesis with these antimicrobial properties would prevent subprosthetic stomatitis and caries formation. Unlike current antifungal therapy aimed at treating the disease, the use of an antifungal prosthesis would have the twofold effect of preventing and treating these pathologies. The antifungal properties of the new prosthesis material based on copper nanoparticles would control the proliferation of microorganisms on the surface of the prosthesis, killing the colonies of the pathogen (fungicidal effect) as well as reducing its adhesion on the surface of the prosthesis (antifouling effect). The antimicrobial conditions provided by the new prosthetic material should considerably reduce the chances of developing these pathologies. Additionally, users who manifest the pathology could replace their conventional dental prostheses with the antimicrobial device, providing a new alternative to treat subprosthetic stomatitis without the inconveniences caused by traditional antifungal therapy.

The prevention of subprosthetic stomatitis would considerably improve the quality of life of prosthesis users, as well as prevent patients from investing in the extra time and expense involved in the dental treatment of the pathology. It would have a particularly significant social impact in the oral health of the large elderly population, as well as in the most vulnerable socioeconomic strata that use removable prostheses as their only alternative for dental rehabilitation.

Removable prostheses are currently the most widely used alternative for the rehabilitation of partially or totally edentulous patients, especially in low-income groups, and are the main form of dental rehabilitation in the country's primary care services. This use of this type of implement is widespread throughout the world in a high percentage of the population. Thus, in countries such as the Netherlands, 19% of the population over the age of 16 use prostheses [Central Bureau of Statistics (Statistics Netherlands), Web magazine, 28 Dec. 2005]. In Spain, this figure reaches an estimated 9 million users (20% of the population) [U&N AC Nielsen, Análisis de Mercados, El Blog de la Salud Bucal (Dentaid), http://www.blogsaludbucal.es/archive/2010/10/25/protesis-dentales-comodas-y-limpias.html (2009)], while in the United States more than 35 million people use total or partial prostheses [The National Center for Health Care Statistics http://www.cdc.gov/nchs/)]. In Chile, the use of dental prostheses is prevalent in 50% of the plans of the "Dental Treatment Flowchart for 60 year-old Adults" of the "Clinical Guide to Comprehensive Oral Health for Adults 60 years of Age" by the Health Ministry (2010). Data from the "National Health Survey" carried out in 2003 shows that more than 60% of the population over 65 years old uses dental prostheses.

As with all foreign elements, prostheses must be well maintained, mainly in terms of their cleaning. This is not always done properly, an occurrence that is more common in the case of the elderly. This deficiency favors the formation of microbial plaque that in many cases generates a swelling of the oral mucosa, whose culture media are the remains of food in the prosthesis. All of this results in the generation of a chronic inflammatory process of the mucosa adjacent to the prosthesis, known as subprosthetic stomatitis. The diagnosis of this pathology is fundamentally clinical and its symptoms are variable, ranging from asymptomatic to pain and/or burning of varying intensity in the compromised oral mucosa. Subprosthetic stomatitis is one of the most frequently diagnosed disorders in oral pathologies and constitutes an oral health problem that requires more effective prevention and/or control alternatives. This pathology can degenerate into a hyperplastic lesion if not readily treated. It usually occurs in the supporting mucosa in patients with removable prostheses, which are commonly kept in poor condition. Subprosthetic stomatitis defines and prevents the optimal use of removable prostheses, as well as the fact that under this clinical condition the user must be treated according to the guidelines with specific topical antifungals, posing a relevant economic burden for the relevant healthcare service. Studies show that the prevalence of subprosthetic stomatitis varies between 25-65% [N. González, I. de Jesus et al., Prevalence of subprosthesis stomatitis, AMC, Camagüey, v. 13, n. 1, Feb. 2009, and Zissis A, Yannikakis S, Harrison A., *Comparison of denture stomatitis prevalence in 2 population groups*, Int J Prosthodont, 2006 November-December; 19(6):621-5], involving subjects whose ages range from 25 to 90 years. The pathology has a prevalence of 40% in people between 50 and 65 years of age, and is predominant in females with a 4:1 ratio [La estomatitis subprotésica, Apuntes de Odontochile, www.odontochile.cl]. Two-thirds of removable prosthesis users are generally considered to suffer from subprosthetic stomatitis to a varying degree.

Although stomatitis can be caused by local factors such as a misaligned prosthesis, an altered immune system or tobacco use, this condition is mainly caused by a microbial infection. It is estimated that a large percentage is the result of an exaggerated response of the body to an infection of the mucosa by microorganisms that colonize the surface of the prosthesis, which in most cases is caused by fungi of the Candida genus. These pathogens are commensal members of the oral microbiota, and are present in about 40 percent of the population without causing problems in most cases. However, their uncontrolled proliferation due to a period of immunosuppression or the presence of local factors, enables the colonization of the patient's tissues. This generates alterations in the oral mucosa that are manifested with a series of symptoms and signs that are generically known as Oral Candidiasis. Chronic Atrophic Candidiasis is a type of oral candidiasis that is directly associated with the use of removable prosthesis, and is different from other types of candidiasis because it occurs in areas that are covered by the appliances, such as the hard palate, appearing as an erythema and edema in the area. Chronic atrophic candidiasis may manifest as well-defined hyperemic macules (Type I), as diffuse erythema of part or all of the area covered by the prosthesis (Type II), or as papillary (granular) hyperplasia involving the hard palate or alveolar ridge (Type III). The most relevant microorganisms responsible for this infection are yeast species of the Candida genus, such as C. glabrata, C. tropicalis, C. kefyr, C. krusei and C. guilliermondii; however, Candida albicans is the most frequently found in oral cavity lesions [Williams D W, Kuriyama T, Silva S, Malic S, Lewis M A (2002), Candida biofilms and oral candidosis: treatment and prevention, Postgrad Med J; 78:455-459]. C. albicans is known to first colonize the back of the tongue and, from there, it is able to invade other sites in the oral cavity such as the mucosa, teeth or dental materials with a secondary colonization [Webb B C, Thomas C J, Willcox M D, Harty D W, Knox K W (2011), Candida-associated denture stomatitis, Aetiology and management: a review. Part 1; Factors influencing distribution of Candida species in the oral cavity, Aust Dent J 39(11):711-9]. C. albicans exhibits the greatest number of virulence factors associated with pathogenicity, including: the ability to adhere to host cells (mucosal adhesion), proteinase secretion (tissue destruction), and changes in morphology from yeasts to pseudohyphae and hyphae. The main mechanism allowing these microorganisms to remain in the oral cavity is through the formation of biofilms on the surfaces. The biofilm protects the yeasts from the mechanical removal action of saliva and acts as a protective barrier against the penetration of host immune response factors as well as administered antimicrobials. Candida initially adheres to surfaces in the form of yeast, then proliferates by growing yeast and generating multi-celled filamentous extensions in the form of hyphae.

The existence of subprosthetic stomatitis not only affects the quality of life of a large part of the population (60% of the 20% of the population that uses dental prostheses), especially the elderly, affecting their normal functions such as chewing, speaking and aesthetics, but also generates a great direct economic cost. This cost is related to the need for extra dental visits, check-ups and treatments that may involve replacing the appliance.

From a national point of view, this pathology requires special planning and the use of additional resources in public health services.

The aforementioned current therapies used to control stomatitis are effective as long as the patients are committed to the treatment and the conditions that allow for the uncontrolled proliferation of microorganisms are modified. However, according to clinical experience, these control measures are generally ignored, which results in a high incidence of this pathology in the Chilean population, reaching 22.3%. The treatment is usually complex and poses a substantial economic cost for patients, as it requires frequent dentist visits, drugs and materials to restore the health of the tissue. If we consider that the main users of this type of appliance are low-income social groups, there is a pressing need to look for alternatives to reduce the incidence of candidiasis caused by the use of removable prostheses.

The treatment of a patient with oral candidiasis usually involves several considerations. As an essential part of the treatment, the patient is instructed in an appropriate hygiene technique to ensure the complete removal of the biofilm, both from the surface of the mucosa as well as from the dental prosthesis. In addition to mechanical biofilm removal procedures, the use of mouthwashes that are active against Candida yeasts such as chlorhexidine and triclosan is recommended. Patients are also strongly encouraged to stop smoking, because tobacco produces a higher incidence of oral candidiasis. The treatment also seeks to detect and correct any dietary deficiencies, such as inappropriate carbohydrate intake. In most patients, these measures may be sufficient to control the infection, but there is a significant percentage in which, despite these interventions, it is impossible to control the disease. This is because there are other factors involved, and they cannot be modified. These include patients with HIV or those who have undergone organ transplants and are being treated with immunosuppressants. In these particular cases, as well as in those in which the pathology is not controlled with the initial measures, the treatment resorts to the use of antifungal agents.

Several antifungals are currently known to be effective in the treatment of candidiasis, such as polyphenols (Nystatin, Amphotericin B), triazoles (Fluconazole, Itraconazole, Voriconazole and Posaconazole), echinocandins (Caspofungin, Micafungin, Anidulafungin), and Fluencytosine. These drugs can be administered topically or systemically. However, the use of antifungals can also cause a number of adverse reactions, such as headaches, nausea, vomiting and general gastrointestinal distress. Due to their elimination mechanism, some systemic drugs may be hepatotoxic, or generate neutropenia. Systemic antifungals usually also interact with other medications, so their prescription requires performing a thorough anamnesis history. Therefore, dentists try to avoid the use of systemic antifungals, and they are only prescribed in clearly justified situations. In the case of less aggressive candidiasis, topical antifungals are the first line of therapy. These substances have a generally favorable response when used in direct contact with the lesion. However, topical administration is often ineffective compared to systemic use, due to the need for frequent application of the drug to the affected surface, which patients oftentimes fail to do. Topical drugs are also known for their unpleasant taste, discomfort during use and short contact with the oral mucosa. On the other hand, several side effects can also occur from the contact of the drug with the lesion.

In this case, the most important ones are the irritation of the mucosa or the skin, alterations in taste and a burning sensation in the area. A recent study published by AL-Dwairi et al. concluded that exposure of prosthetic acrylic (PMMA) to topical antifungals may also affect the roughness, wettability and free surface energy of the prosthetic material. The results of this study show that the changes produced by the antifungal in acrylic paradoxically increase the adhesion of *C. albicans* to the material.

In short, the high impact of this pathology and the growth that is predicted due to the constant increase in the most vulnerable population such as the elderly, means that there is a demand for innovative solutions to curb this problem. Within this context, there is an opportunity to develop a new type of prosthesis containing antimicrobial agents to help minimize the prevalence of this disease. Thus, the development of new resins with copper particles is proposed, in order to generate materials that are able to release the active agent (metallic ions) in a controlled manner to prevent the development of this pathology.

The development of copper-based antimicrobial resins presents a scientific and technological challenge from several perspectives. The challenge is based on the need to develop nanometric or nanostructured copper particles that remain stable in the polymer matrix used in dental prostheses. To achieve this, it is necessary to find the best copper nanoparticle to incorporate as well as the best methodology to prepare the polymer composite. Furthermore, this compound must also have a controlled release of copper ions at a rate that is less than the minimum required to avoid toxicity and close to the concentrations necessary for it to have a biocidal effect. All of the above, without altering the polymerization and/or curing process of the resin, or the current commercial preparation process of the prosthesis. From a technological point of view, the new prosthesis must maintain the structural properties of the original resin, without substantial alteration in its color or aesthetics. This poses new challenges related to the type of copper particle, concentration, and its distribution in the polymer matrix.

The present invention concerns the development of an antimicrobial material for prostheses, using elements and techniques currently offered by nanotechnology. In particular, the use of metallic copper with nanometric particle size, unlike the use of the most traditionally studied copper ion salts. The new antifungal material corresponds to a nanocomposite, i.e. a composite material that combines materials of different natures in which one of them has nanometric dimensions. The preparation of this nanocomposite using the current acrylic prosthesis as the polymeric matrix and the nanometric copper particles (CuNPs) as the antimicrobial component, constitutes the central aspect of the invention.

The preparation of this nanocomposite material considers finding the most suitable conditions for the incorporation of the CuNPs in the matrix, combined with the antimicrobial, aesthetic (color), mechanical and cytocompatibility properties of the resulting material. The most traditional method to prepare polymeric nanocomposites is to physically mix the melted or dissolved polymer in a solvent with the nanoparticles (ex situ method). The manufacture of a dental prosthesis is a polymerization process that occurs on a disposable material, which has the dental record of the patient, given by the position of artificial teeth. Thus, the use of the ex situ method would require dissolving existing dentures and is therefore not feasible for this application.

In a previous study carried out by the inventors (Correa, S., *Preparación de Resinas Acrilicas cargadas con nanoparticulas de cobre y sus propiedades antimicrobianas frente a Candida Albicans*, Instituto de Ciencias Odontológicas. 2012, Universidad de Chile: Santiago de Chile), the incorporation of CuNP in acrylic of dental prostheses was researched. In this study, methyl methacrylate monomer and an organic solvent were used as reducing agents to allow the in situ formation of copper nanoparticles during the self-cure acrylic polymerization process. It was observed that the nanocomposite acrylic material loaded with CuNPs, has a marked antimicrobial activity against the *Candida albicans* species, inhibiting the growth of *Candida albicans* in the prosthetic material by 80% in comparison to the control group. This effect was proportional to the content of CuNPs in the composite. The antimicrobial effect of acrylic (CuNP/PMMA) was sustained over time, suggesting that CuNPs and/or copper ions are gradually released into the environment [31]. The method developed, as well as the new material, appears to be a promising alternative for the control of subprosthetic infections caused by *Candida albicans*. Furthermore, the presence of copper in the prosthetic material may also control the development of periodontal pathogens. Previous studies by our laboratory group have developed biopolymer gels charged with copper nanoparticles, which are capable of inhibiting the growth of *Aggregatibacter actinomycetemcomitans*. (González, J. P., *Sintesis de materiales bactericidas basados en nanoparticulas metálicas y biopollmeros para terapia periodontal odontológica*. Instituto de Ciencias Odontológicas. 2013, Universidad de Chile: Santiago de Chile).

This suggests that the presence of copper nanoparticles in acrylic, and therefore their interaction with the oral cavity, may reduce the growth of periodontal pathogens.

The development of copper-based antimicrobial resins presents a scientific and technological challenge from several perspectives. The challenge is based on the need to develop nanometric or nanostructured copper particles that remain stable in the polymer matrix used in dental prostheses. This is achieved by finding the best copper nanoparticle to incorporate as well as the best methodology to prepare the polymer composite. Furthermore, this compound must also have a controlled release of copper ions at a rate that is less than the minimum required to avoid toxicity and close to the concentrations necessary for it to have a biocidal effect. All of the above, without altering the polymerization process of the resin in the current commercial preparation process of the prostheses. In the previous thesis study, we worked with self-curing acrylics, so our work proposes the optimization of the nanocomposite preparation process under heat-curing conditions, which is the process used commercially for the manufacture of dental prostheses. A comparison of the previously developed in-situ process with the traditional ex-situ process method will also be considered. In the latter procedure, the CuNP is pre-synthesized by another technique and then added to the polymer matrix. This new material has antimicrobial properties against *Candida albicans*, inhibiting their growth and thus preventing or treating subprosthetic stomatitis. The new prosthetic material is also expected to exhibit antimicrobial activity against periodontal pathogens. The latter could have consequences in controlling periodontal infections in partially edentulous patients (prosthesis wearers), and thus stimulate the periodontal health of the remaining teeth, improving their oral prognosis. On the other hand, the new prostheses must keep the structural properties of the original resin, without any substantial alterations in their color from an aesthetic-dental point of view. This suggests the need to optimize the preparation process of the nanocomposite prosthesis material according to the different properties (antimicrobial, mechanical, color) related to the type of copper particle, concentration, incorporation method and its distribution in the polymer matrix among other variables.

The present invention focuses on the preparation of a nanocomposite material based on copper nanoparticles and thermo-cured polymethylmethacrylate with antimicrobial properties against *Candida albicans*, optimizing its mechanical, cytocompatibility and aesthetic properties. It uses an in-situ method of nanocomposite formation, incorporating the nanoparticles during the polymerization process. In this case, the previously synthesized particles are incorporated by dispersing them in one of the components of the reaction (monomers, solvent), allowing polymerization to occur thereafter. The invention not only proposes an on-site preparation of the nanocomposite, but for CuNPS to also be synthesized during the polymerization process. This process is based on the reducing properties of methyl methacrylate monomer, which could be enhanced by the addition of small fractions of some organic solvent, such as ethanol. Thus CuNPs can be formed by the monomer's reducing action on copper ions incorporated from a metal salt. This type of in-situ formation process of the nanoparticle allows for a more efficient incorporation and a more homogeneous dispersion of the particle in the nanocomposite matrix. These aspects are known factors that favor the bioactive, mechanical and optical properties (color) of the resulting composite. The invention also considers the preparation of the nanocomposite, using CuNPs previously synthesized by other methods. In this case, commercially available CuNPs will be used, as well as CuNPs enveloped on particles of a ceramic material. The second approach is also a major contribution from a scientific standpoint.

Copper enveloped on ceramic matrices has on average a lower density and a lower impact on the staining of polymer composites.

Furthermore, as part of the development of the present invention, a method has been devised to synthesize CuNPs on nanostructured ceramic materials, such as zeolites or silica.

Zeolites are crystalline aluminosilicates with a nanostructure made up of pores, channels and crevices with sub-nanometric dimensions. A copper-zeolite material can be obtained thus, where the nanoparticles of the metal are enveloped in the crevices of the ceramic material. The process of CuNP synthesis enveloped on ceramic particles uses biocompatible reducing agents, which makes these materials particularly suitable for biomedical applications.

Since the prior art does not report studies of dental acrylic preparation with CuNPs, all techniques and strategies of synthesis for the preparation of dental acrylics with antimicrobial properties are of interest. The application of these procedures extends to any type of dental acrylic resins, such as those used in restoration composites, restoration adhesives, orthodontic adhesives, sealants, or ionomer glasses; applications in which antimicrobial control is currently of interest.

Dental prostheses made of the nanocomposite material have a pronounced antimicrobial effect against *C. albicans* and *Streptococcus mutans* due to the renowned antimicrobial properties of copper, especially because it is an effective antifungal. According to the principles of nanotechnology, nanometric-sized copper particles should present a higher activity, which means that low metal contents can produce a significant antimicrobial effect. The antifungal properties of the nanocomposite are given by the fungicide or anti-fouling effect of copper. These effects are produced by a controlled release of copper particles from the polymeric matrix when the nanocomposite is exposed to an aqueous medium. Polymer matrices oftentimes suffer from erosion when in contact with the physiological environment, which also facilitates the release of copper from the surface of the nanocomposite. Furthermore, it has been demonstrated that water molecules can penetrate between the polymer chains, oxidizing the nanoparticles, producing their diffusion and subsequent release from the polymer matrix in the form of ions. The use of different advanced characterization techniques such as XPS, complemented with studies on copper release in aqueous mediums and microbiological tests, allow us to achieve a better understanding of the antifungal effect of the new material.

Current solutions to the problem of subcutaneous stomatitis focus mainly on the application of topical antifungals to the affected mucosa. Although treatment with antifungals may alleviate the infection, many patients, especially the elderly, often fail to properly follow topical application procedures. Topical antifungals are also known to have an unpleasant taste, to generate discomfort during use and for their short-lived contact with the oral mucosa. Due to the disadvantages of topical antifungals, as well as the limitations exhibited by patients in following antifungal application protocols, new alternatives are required to address this oral health problem.

Strategies aimed at preventing the development of the disease are always more advisable in terms of public health. Therefore, the development of dental prostheses with antimicrobial properties seems to be an attractive alternative to control oral infections. A dental appliance made of a material specially formulated to have an antimicrobial effect against *C. albicans* should significantly reduce the occurrence of stomatitis caused by said pathogen. That is why the most recent advances in nanotechnology are being used to develop new prosthetic materials. This field, which studies the control of matter at a nanometric scale ($10^{-9}$ m) to generate products with improved or new properties, is making its mark in several areas of industrial and social impact worldwide. In the dental field, the influence of nanomaterials can be found, for example, in today's nanocomposite resins for dental restorations, which are more durable and have improved aesthetic properties.

In recent years, copper nanoparticles have been found to be more effective as antimicrobial agents than microparticles, opening up opportunities in nanotechnology in the field of antimicrobial materials. This justifies the use of these particles as agents to be included in plastic matrices, as seen in other systems such as polymer/silver. Although the antimicrobial properties of nanometric copper are well-known in other spheres of application, its use in dental products is still unknown, thereby constituting a novel and innovative research component of this proposal.

The antimicrobial material consists of a nanocomposite, a composite material that combines different materials (polymer and metal) whereby some of them have nanometric dimensions. The nanocomposite consists of a polymethylmethacrylate matrix (PMMA) that disperses several copper nanoparticles (CuNPs). The selection of the matrix is based on its widespread use in prosthesis applications, so as to facilitate its marketability.

The present invention focuses on developing the most suitable technology to manufacture the nanocomposite material, combining the preparation variables with its antimicrobial properties against *C. albicans*; as well as with its mechanical and aesthetic characteristics. The process of nanocomposite formation considers in-situ synthesis of CuNPs during PMMA polymerization, although an alternate ex-situ addition of metal particles is also considered, changing the charge ratio in the matrix. The objective is to find the best particle, its content in the polymeric stock and the most appropriate method for its incorporation, taking into account the antimicrobial, aesthetic and mechanical behavior of the resulting nanocomposite material.

FIG. 1 shows the preparation process of the nanocomposite. The in-situ (on-site) process uses a copper salt as a precursor to the CuNPs, while the ex-situ (off-site) processes use pure powdered CuNPs or a ceramic material such as zeolite or copper-modified silica. In general, in the in-situ method, the CuNP precursor is incorporated into the monomer, and then mixed with the polymer according to the traditional procedure to prepare the prosthesis acrylic and produce polymerization by self or thermal curing. These different methodologies make it possible to optimize the process of obtaining the antimicrobial resin in order to find the best formulation. They are also the basis of the innovation introduced by the present invention, since they consider different aspects, such as coloring. On average, copper in an inorganic matrix exhibits a particularly low density and less impact on coloring.

The addition of copper nanoparticles to the resin currently used in prostheses is expected to generate a new antimicrobial material with similar aesthetic and mechanical properties to existing resins in use today. This is because copper is an effective antimicrobial agent and its nanoparticles are more effective than its microparticles. Also, as the particles are nanometric in size, they do not significantly affect the performance of the original matrix. All of the foregoing justifies our nanotechnology-based approach.

Figure 2:
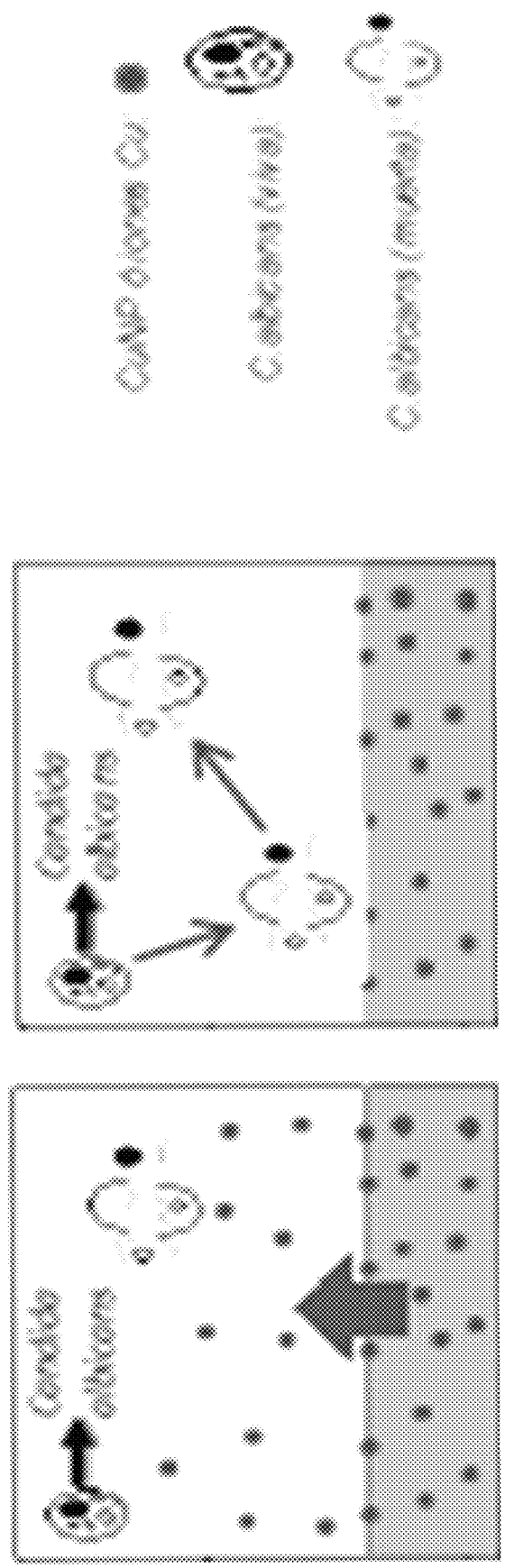
FIG. 2 illustrates a possible antifungal action mechanisms of a CuNP/PMMA nanocomposite.

FIG. 2 illustrates possible antifungal action mechanisms of the CuNP/PMMA nanocomposite. The antimicrobial action mechanism of the new nanocomposite material has been observed to occur mainly through the release of copper ions into the environment (FIG. 2). Ions are released in a sustained manner from within the polymer matrix, exerting a fungicidal action on existing microorganisms that come into contact with the surface of the material or are located near the interface. This mechanism reduces the viability and adhesion of the pathogen on the surface of the prosthetic material as well as on the mucosa in contact with the dental appliance. These properties of the new prosthetic material provide the antimicrobial conditions to prevent or treat subprosthetic infection.

With regard to existing regulations for the use of copper in humans, the Food and Drug Administration (FDA) considers maximum levels of copper in bottled water for consumption of 1 mg/mL (FDA 2001a). On the other hand, the Institute of Occupational Medicine (IOM) reports a Recommended Allowed Diet (RDA) of 0.9 mg/day, as well as a maximum tolerable intake of 10 mg/day. In the present invention, nanocomposites have a copper content of approximately 30-150 μg/g. The acrylic material of a prosthesis base has a mass of approximately 10 g, so a prosthesis made from the nanocomposite will have a maximum copper content of 0.3-1.5 mg. This suggests that the amount of copper released into the oral cavity will be below the levels recommended in some of the regulations. Cytoxicity studies were also carried out on each of the formulated materials, in order to optimize the antimicrobial activity of the nanocomposite in line with bio-tolerable copper levels as per the existing regulations.

From a methodological standpoint, the composite material is synthesized using different in-situ synthesis strategies. In such strategies, copper, either as a precursor to the subsequent nanoparticle or as an already synthesized particle, is mixed with the monomer to perform the polymerization together. In the first strategy, both the polymer and the nanoparticle are synthesized in the same stage by adding a copper precursor and the monomer; in the second strategy, the already synthesized nanoparticle is mixed with the monomer for subsequent polymerization. In the latter strategy, two forms of copper nanoparticles were studied: metallic and copper enveloped in a ceramic matrix.

Given that antimicrobial effectiveness and toxicity are related to the release of copper ions, we seek to find the methodology that best controls the rate of release of ions, without altering the polymerization process or the final properties of the resin: mechanical, aesthetic (staining) and cytocompatibility.

DETAILED DESCRIPTION OF THE FIGURES

FIG. 3A shows a SEM microscopic image of copper nanoparticles (CuNP) synthesized in-situ in the acrylic monomer, where the average size of CuNP is 40 nm and their nanometric nature was also confirmed by the surface resonant plasmon detected by the characteristic absorption band at 593 nm (see FIG. 3B).

FIG. 3B shows a SEM image of copper nanoparticles synthesized by the in-situ method in acrylic monomer (a) and an absorption spectrum indicating the surface resonant plasmon.

FIGS. 4A, 4B and 4C illustrate the presence of copper nanoparticles in the nanocomposite acrylic matrix. This was confirmed by EDX elemental mapping, finding a relatively homogeneous distribution of the metal over the entire polymer matrix. The FTIR analysis of the materials indicated that the nanocomposite spectra feature all the bands corresponding to the PMMA spectrum, indicating that the chemical structure of the polymer is unaffected by the incorporation of metal nanoparticles. FIG. 4A shows a SEM image of CuNP/PMMA nanocomposite, FIG. 4B shows an EDX elemental mapping confirming the distribution of copper in the acrylic matrix; and FIG. 4C shows an FTIR-ATR analysis of PMMA acrylic and nanocomposite materials.

Figure 5A:
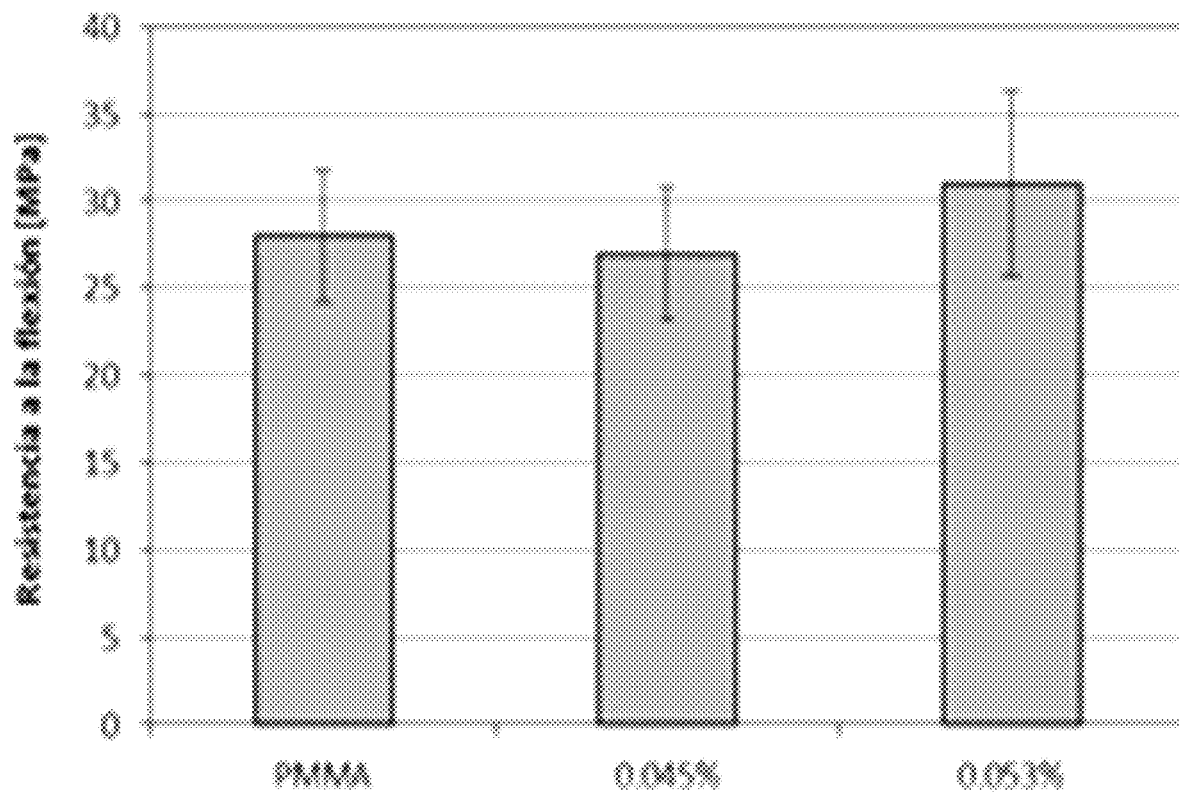
FIGS. 5A and 5B illustrate that nanocomposites with different CuNP contents maintain the original mechanical properties of PMMA acrylic control.
Figure 5B:
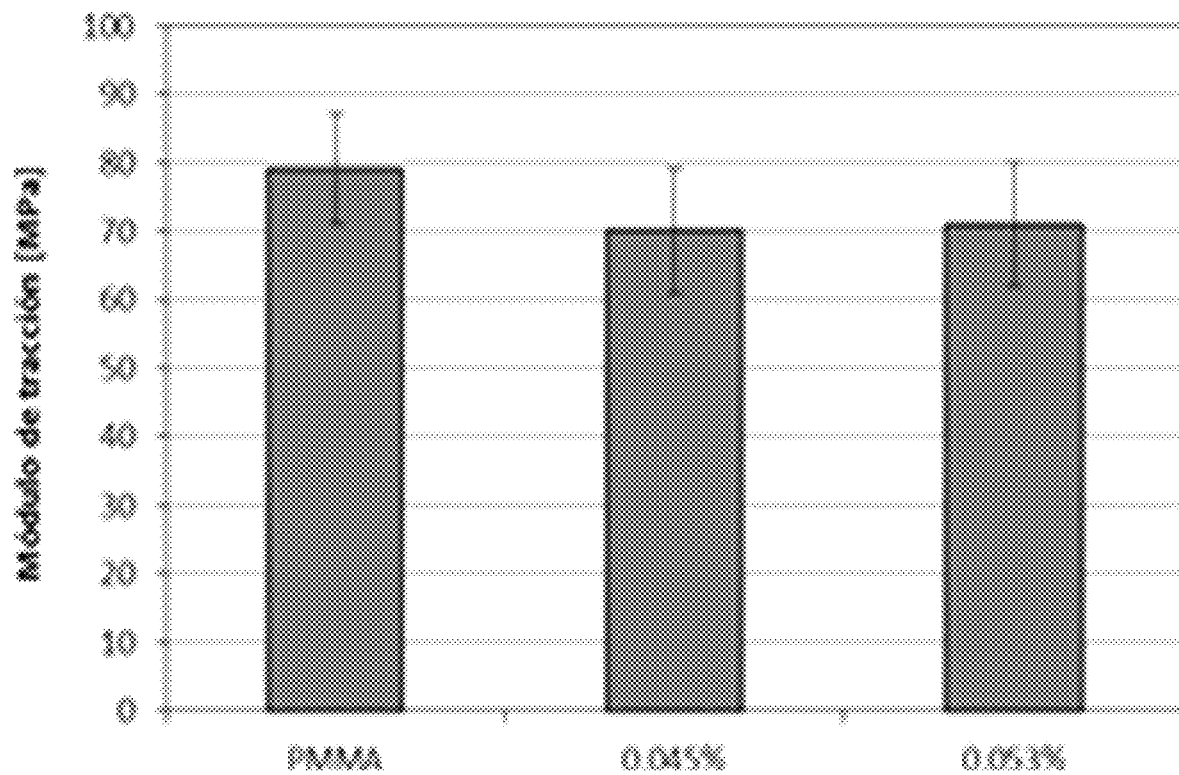

FIGS. 5A and 5B show that nanocomposites with different CuNP contents maintain the original mechanical properties of PMMA acrylic control. FIG. 5A shows the mechanical bending strength property of PMMA acrylic and nanocomposites with different CuNP content; and FIG. 5B shows the mechanical property of the compression module of PMMA acrylic and nanocomposites with different CuNP content:

The results of the antimicrobial activity of the nanocomposites against C. albicans was expressed as an ability to inhibit the growth of the microorganism on its surface with respect to the number of colonies grown in the non-CNP PMMA control material, which is defined by the following expression:

$$\text{Inhibitory capacity} = \frac{CFU_{PMMA} - CFU_{CuNP/PMMA}}{CFU_{PMMA}} \times 100$$

$CFU_{PMMA}$: Colony-forming units grown on the acrylic surface of PMMA.

$CFU_{PMMA}$: Colony-forming units grown on the surface of the CuNP/PMMA nanocomposite.

Figure 6:
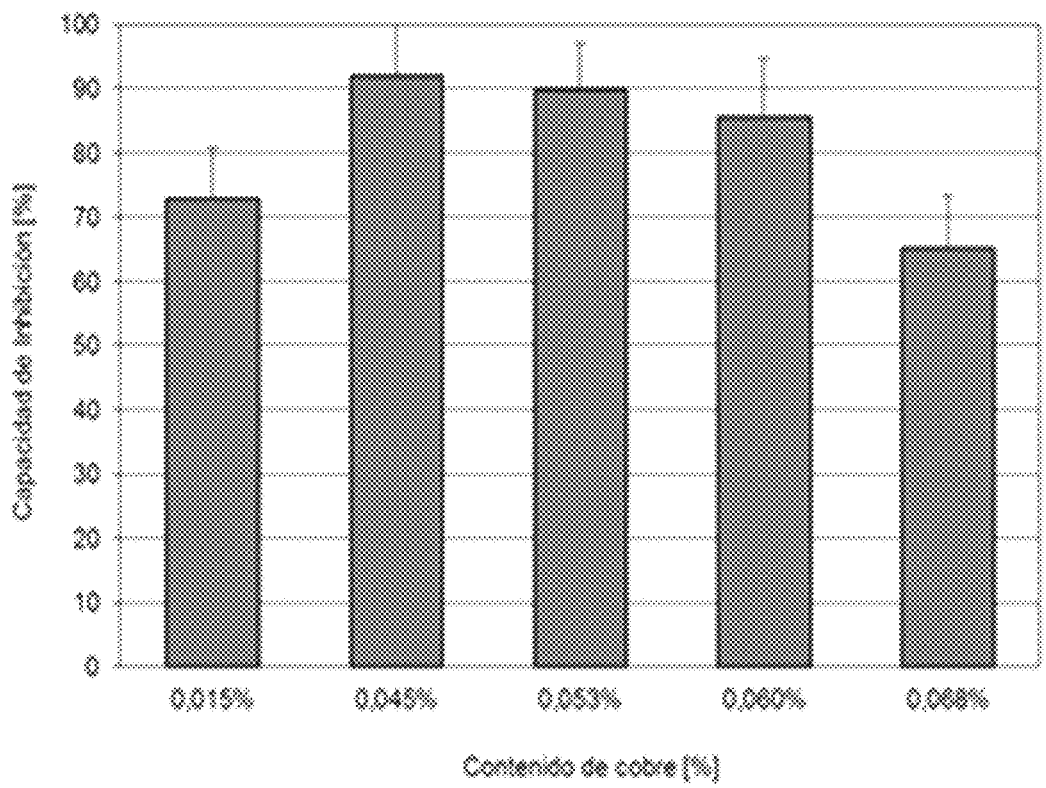
FIG. 6 illustrates the inhibition capacity of nanocomposites against *C. albicans* after 48 hours of incubation prepared with different CuNP contents.

FIG. 6 shows the inhibition capacity of nanocomposites against C. albicans after 48 hours of incubation prepared with different CuNP contents, in which it is observed that prepared prosthesis acrylic nanocomposites have a copper content range between 0.015 and 0.068%, and which produce an inhibition percentage range between 65% and 92%, where the maximum inhibition capacity of the growth of *C. albicans* is obtained with a CuNP content of 0.0455%.

Figure 7:
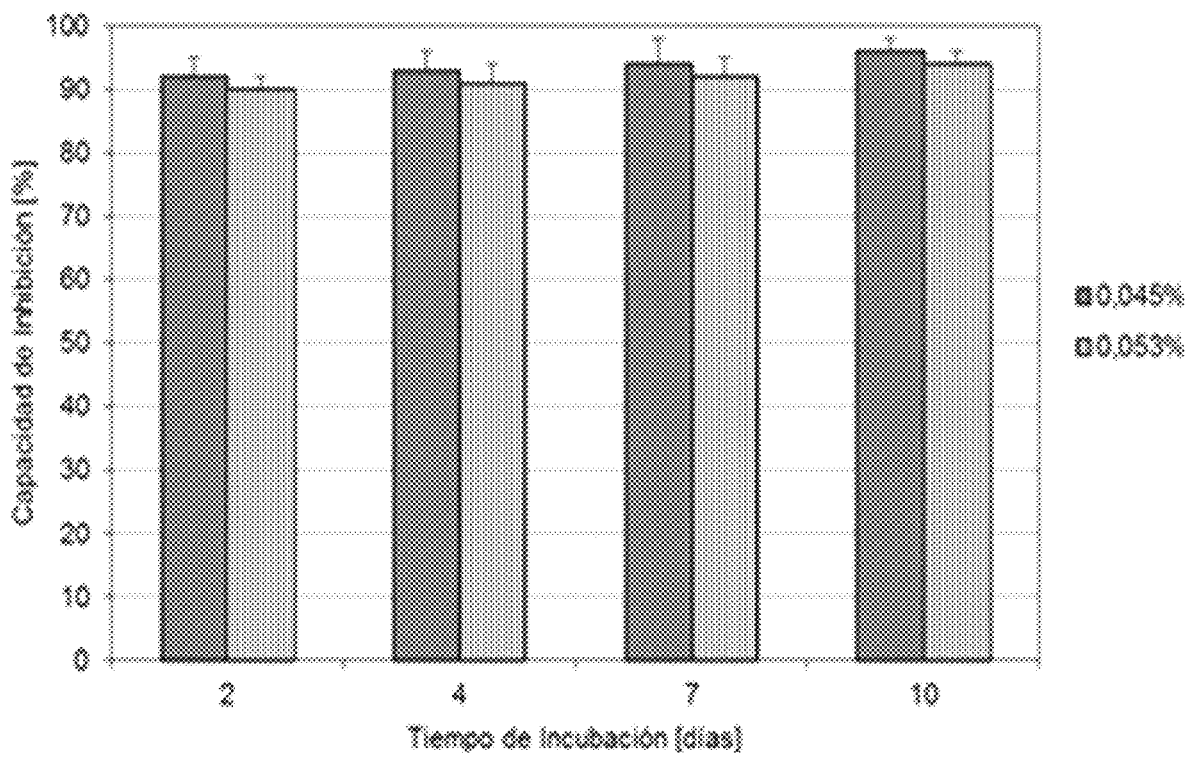
FIG. 7 illustrates the inhibition capacity of nanocomposites (CuNP/PMMA) against *C. Albicans* at different incubation times.

FIG. 7 shows the inhibition capacity of nanocomposites (CuNP/PMMA) against *C. albicans* at different incubation times, where it was found that the antimicrobial effect on the surface of the material is prolonged over time.

Figure 8:
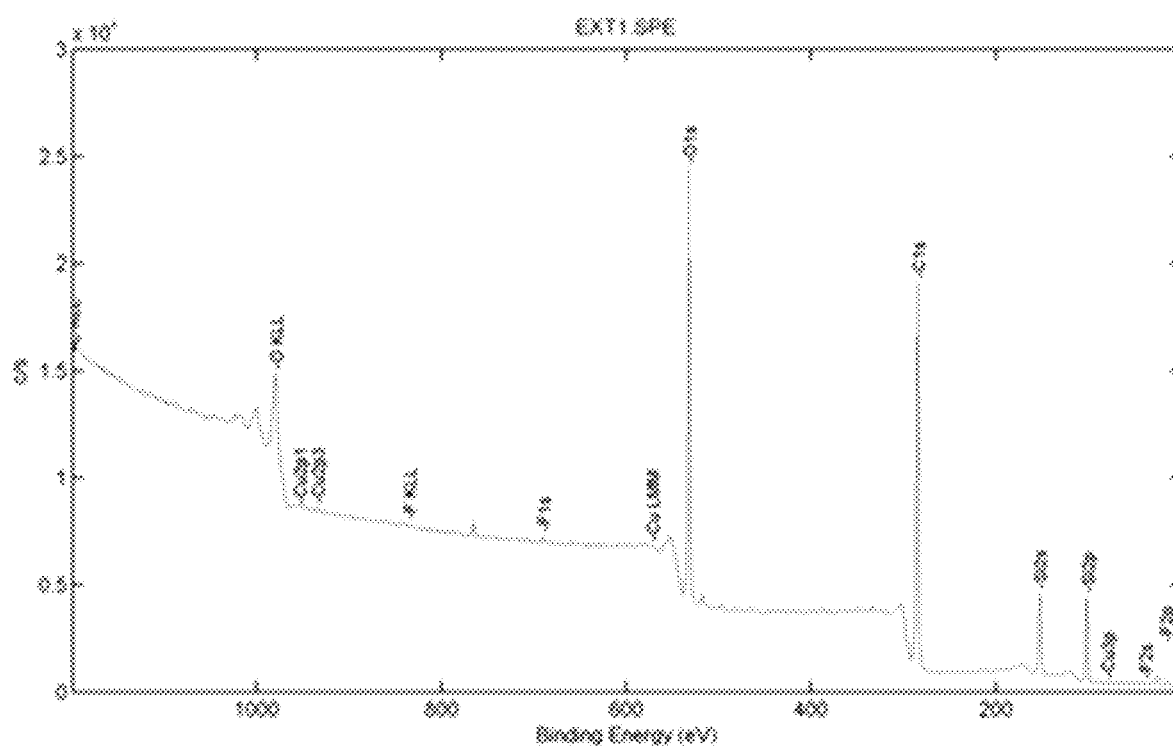
FIG. 8 illustrates an XPS spectrum of the surface of the naocomposite acrylic CuNP(0.045%)/PMMA.

In order to elucidate the possible mechanism of antimicrobial action of the nanocomposite material, the surface of the material was analyzed by XPS spectroscopy. FIG. 8 shows the XPS spectrum of the surface of the nanocomposite acrylic CuNP(0.045%)/PMMA. The results of the analysis indicate that there are no detectable copper atoms on the surface of the material; therefore, the antimicrobial effect should be attributed primarily to the amounts of copper released into the medium as a result of the diffusion of copper ions or nanoparticles from the acrylic matrix into the medium.

Figure 9:
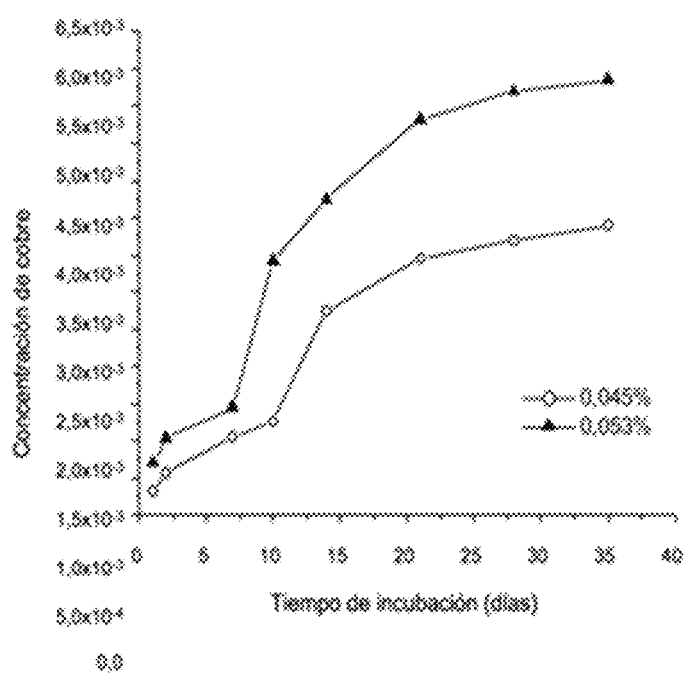
FIG. 9 illustrates the time-dependent release of copper from nanocomposite acrylic in artificial saliva (pH 6.5).

FIG. 9 shows the time-dependent release of copper from nanocomposite acrylic in artificial saliva (pH 6.5), where it is observed that the materials release very low concentrations of copper to the medium, with maximum values around $5.8 \times 10\text{-}3$ μg/mL after 35 days of incubation in artificial saliva. However, these low levels of copper release are sufficient to produce the observed antimicrobial effect while maintaining the biocompatibility of the new prosthetic material.

Figure 10:
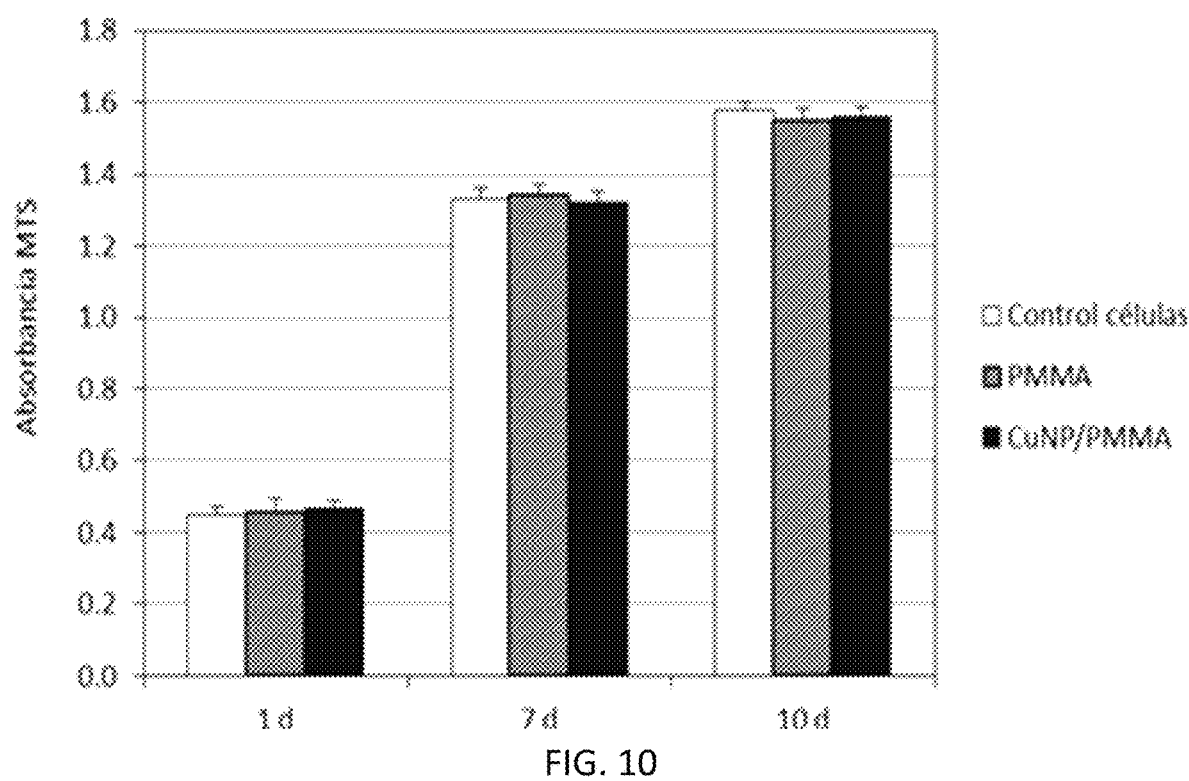
FIG. 10 illustrates the viability of human fibroblastic cells cultured at different incubation times.

FIG. 10 shows the viability of human fibroblastic cells cultured at different incubation times with the current acrylic prosthetic material (PMMA) and the CuNP/PMMA nanocomposite measured by the MTS mitochondrial activity assay. It can be observed that the cell viability on the CuNP/PMMA nanocomposite is equivalent to that observed on the current PMMA acrylic prosthesis. These results demonstrate that the incorporation of CuNPs in acrylic does not alter its cytocompatibility characteristics.

The preparation process for antimicrobial acrylics can also be extended to various acrylic materials for dental use, such as dental restoration resins, adhesives for restoration resins or orthodontic brackets, occlusal pit and fissure sealants as well as resin-modified ionomer glasses. These materials are prepared using acrylic monomers other than MMA, such as Bis-GMA, TEGDMA, UDMA, HEMA or PENTA and can be polymerized by photo-, self- or dual curing. TABLE 1 shows the inhibition capabilities of the cariogenic bacterium *S. mutans* for the various dental nanocomposites prepared using the ex situ process of incorporation of CuNPs.

TABLE 1

| Material Dental | Capacidad de inhibición de *S. mutans* (%) ± DS |
|---|---|
| Acrílico de prótesis | 97 ± 2 |
| Resina dental restauración | 97 ± 2 |
| Adhesivo dental | 99 ± 3 |
| Sellante dental | 99 ± 3 |
| Vidrio ionómero | 95 + 4 |

The CuNP/PMMA dental acrylic nanocomposite also exhibited inhibitory activity against the bacterium *Agreggatibacter actinomycetemcomitans* (93%±3), a typical pathogen of gingivitis and periodontitis.

The preparation process of the CuNP/PMMA nanocomposite can also be used for the manufacture of bone cement with antimicrobial properties. Self-healing PMMA-based bone cement is used in orthopaedics to attach hip, knee, shoulder and other joint prostheses. Bone cement based on CuNP/PMMA had an inhibitory capacity of 94%±3% against *Staphylococcus aureus* bacteria, the main pathogen responsible for periprothesic infections.

The present invention is geared towards developing a polymeric material with copper nanoparticles (CuNP), in which the composite material has been synthesized using different ex-situ and in-situ synthesis strategies. The composite can be prepared by the ex-situ method, incorporating CuNPs/Zeo particles or copper nanoparticles (CuNPs) prepared ex-situ by this or other methods.

In all these strategies, copper, either as a precursor of the subsequent nanoparticle or as an already synthesized particle, is mixed with the monomer (PMMA) to achieve polymerization together. In a first strategy, both the polymer and the nanoparticle were synthesized at the same time by adding a precursor of an organic copper salt [Cu(CH$_3$COO)$_2$] and the monomer; in the second strategy, the synthesized nanoparticle was mixed with the monomer for subsequent polymerization. The latter strategy seeks to study two forms of copper nanoparticles: metallic and copper enveloped in a ceramic matrix. Because antimicrobial effectiveness and toxicity are related to the release of copper ions, the aim is to find the methodology that best controls the rate of ion release, without altering the polymerization process or the final properties of the resin, such as mechanical, aesthetic (staining) and cytocompatibility.

EXAMPLES

Example 1

In this example, the preparation of CuNP/PMMA nanocomposites consists of an in-situ synthesis of the nanocomposite material using either self- or heat-curing polymerization. Aqueous solutions of copper acetate [Cu(CH$_3$COO)$_2$] of different concentrations (0.1-0.8 M) are used, preferably between 0.6-0.7 M, for which 100 μL of the copper solution (Cu$^{2+}$) is added over 2 mL of absolute ethanol. The resulting mixture is added 2 mL of the self- or heat-cured liquid methyl methacrylate dental monomer under constant agitation. The resulting solution is kept under constant agitation at temperatures between 50-70° C. until nanoparticles form (CuNP), which can be seen by the reddish coloration of the reaction mixture. This liquid monomer solution loaded with CuNPs is then mixed with dental acrylic powder in a 3:2 ratio of acrylic mass:monomer volume (PMMA) to carry out the polymerization reaction under self- or heat-curing conditions as appropriate.

Example 2

In this example, the preparation of CuNP/PMMA composites consists in the use of enveloped CuNPS. The composite material was prepared using CuNPs previously enveloped in ceramic material particles. The use of CuNPs included in ceramic particles could improve the staining properties of the composite as well as provide different copper release kinetics from the material. Furthermore, the ceramic nature of the support makes its density lower than that of metallic particles, helping to address stability and decantation problems. Zeolite particles (nanoporous crystalline aluminosilicate) and silica nanoparticles were used as support materials, using natural zeolite of national origin (MOR) and commercial 100 nm silica nanoparticles. CuNPs are formed on site in the material, whereby a certain MOR mass was contacted with a 0.1 M copper acetate solution for 24 h at room temperature. Once the ion exchange period was completed, the zeolite was separated and washed by repeated centrifugation/dispersion cycles. The resulting material was then dispersed in a starch/ascorbic acid reducing solution and microwaved for a few seconds.

This system for the formation of CuNPs in biopolymers was developed by our laboratory team under the concept of "Green Chemistry", with the aim of synthesizing more benign metallic nanoparticles that are compatible with biomedical applications. The CuNPs/MOR particles were separated, washed and dried for further use in the preparation process of the CuNP/PMMA composite. The composite was prepared using the aforementioned ex-situ method, adding the dehydrated CuNPs/MOR particles to the liquid methylmethacrylate monomer.

Example 3

In this example, the preparation of CuNP/PMMA composites consists of an ex-situ method to incorporate CuNP in self- or thermo-cured dental acrylics, using commercially available 5 nm CuNPs in powder form (Nanotec SpA, Chile). The CuNPs were added to the liquid self- or thermo-cured methyl methacrylate monomer (4 mL). CuNPs masses were in the range of 0.79-6.28 mg, dispersed in ultrasound for 10 minutes and then mixed with dental acrylic powder in a proportion of 3:2 acrylic mass/monomer volume (polymethylmethacrylate with incorporated initiator) to achieve the polymerization reaction. Polymerization was subsequently performed under self- or thermo-curing conditions.

Example 4

This example consists of an in-vitro assessment of the antimicrobial properties of CuNPs/PMMA nanocomposites. This was achieved by conducting a microbiological study on culture broths of the ATCC 90029 strain of *Candida albicans* with a concentration of 0.5 Mcfarland ($1-5 \times 10^6$ CFU/ml). Samples of the CuNPs/PMMA nanocomposite material prepared with various CuNPs contents were incubated in the microorganism suspension, as well as samples of the CuNPs-free acrylic material as control (PMMA). The incubation period was initially 48 hours at 37° C. under aerobic conditions. The antimicrobial effect of the materials was assessed by counting colonies in the supernatant broth as well as on the surface of the materials. In the former case, dilutions of the culture medium were sown on Sabouraud agar plates and incubated for 48 h at 37° C. In the latter, the microorganisms on the surface of the material were removed with a harmless surfactant solution and then sown and incubated in agar before performing the CFU count. The antimicrobial effect of the materials was also assessed for a prolonged period of 10 days in contact with the microorganisms.

Example 5

In this example, the release of copper from the material was tested to explain the nanocomposite's antimicrobial activity mechanism. These tests were performed by immersing one piece of each type of CuNP/PMMA nanocomposite in artificial saliva ($KCl-NaCl-CaCl_2$)-$2H_2O-NaH_2O-Na_2S$-$9H_2PO_4-2H_2O-Na_2S-9H_2O$-urea) pH 6.5 at 37° C. A sample of the supernatant liquid was collected at certain time intervals and replaced with fresh artificial saliva. The total copper concentration in the collected aliquots was determined by inductively coupled plasma atomic emission spectrometry (ICP-AES). From these concentrations, the amounts of metal released were determined as a function of time.

Example 6

In this example, the cytocompatibility of nanocomposites was tested by incubation in fibroblast cell cultures. Cell viability was determined by the MTS mitochondrial activity spectrophotometric assay (3-(4,5-dimethylthiazole-2-yl) 5-(3-carboxymethoxyphenyl)-2-(4-sulphophenyl)-2H-tetrazolium), during 3, 5 and 10 days of incubation with the material.

Example 7

In this example, dental prostheses were manufactured using a nanocomposite material that had been previously optimized in terms of its composition, antimicrobial, mechanical, aesthetic (color) and cytocompatibility properties. Two different manufacturing protocols commonly used by dental laboratories were used for this purpose. The prostheses were manufactured in dental laboratory facilities, under established protocols regarding temperature, and heat-curing time and pressure conditions; as well as the type of trays, printing materials, muffles, and other elements used to design prostheses according to the individual characteristics of each patient. The manufactured prostheses were examined in accordance with dental criteria in terms of the mechanical properties of the acrylic base, stability of the artificial teeth, aesthetic characteristics, among others.

Example 8

In this example, the preparation of CuNP/PMMA nanocomposites consists of an ex-situ method to incorporate CuNPs into dental restoration resins. Powdered CuNPs are added to a photo- or dual curing system based on acrylic monomers, such as Bis-GMA, TEGDMA, UDMA or others, which may contain ceramic particle-based micro or nanofillers. CuNPs concentrations are added, preferably in a range of 0.015-0.045% by weight. The resulting mixture is treated with ultrasound for 10 minutes, and the polymerization reaction is subsequently carried out by applying an L.E.D. light for 40 seconds in the presence of camphorquinone as a photoinitiator.

Example 9

In this example, the preparation of CuNP/PMMA nanocomposites consists of an ex-situ method to incorporate CuNPs into a dental restoration resin bonding system. Powdered CuNPs are incorporated into adhesive systems based on acrylic monomers such as photo- or dual cured UDMA or PENTA. CuNPs concentrations are preferably added in a range of 0.015-0.045% by weight. The resulting mixture is treated with ultrasound for 30 seconds and then polymerized by applying an L.E.D. light for 10-30 seconds in the presence of camphorquinone as a photoinitiator, or by dual-curing polymerization.

Example 10

In this example, the preparation of CuNP/PMMA nanocomposites consists of an ex-situ method to incorporate CuNPs in orthodontic adhesive acrylics. Powdered CuNPs are incorporated into adhesive systems to cement orthodontic brackets based on acrylic monomers, such as TEGDMA, Bis-GMA, UDMA, or photo or self-curing HEMA. CuNPs concentrations are preferably added in a range of 0.015-0.045% by weight. The resulting mixture is treated with ultrasound for 30 seconds and then polymerized by applying an L.E.D. light for 10 seconds in the presence of camphorquinone as a photoinitiator or by self-curing.

Example 11

In this example, the preparation of CuNP/PMMA nanocomposites consists of an ex-situ method to incorporate CuNPs into a light-curing acrylic resin-modified ionomer glass as a cementing and restorative agent in temporary teeth, and as a provisional agent in permanent teeth. CuNPs in powder form are incorporated into the photo or self-cured liquid ionomer glass at preferred concentrations in the range of 0.015-0.045% by weight. The resulting mixture is treated with ultrasound for 30 seconds, and the polymerization reaction is subsequently performed by applying an L.E.D. light for 10-30 seconds in the presence of camphorquinone as a photoinitiator, or through self-curing polymerization.

Example 12

In this example, the preparation of CuNP/PMMA nanocomposites consists of an ex-situ method to incorporate CuNPs into pit and fissure sealants applied to occlusal surfaces of molar teeth, which are particularly prone to bacterial plaque buildup and subsequent caries development. CuNPs in powder form are added to sealing glass based on acrylic monomers such as Bis-GMA or photo or self-curing TEGDMA at preferred concentrations in the range of 0.015-0.045% by weight. The resulting mixture is treated with ultrasound for 30 seconds and then polymerized by applying an L.E.D. light for 10-30 seconds in the presence of camphorquinone as a photoinitiator, or by self-curing polymerization.

Example 13

In this example, the preparation of CuNP/PMMA nanocomposites consists of an ex-situ method to incorporate CuNPs in bone cement acrylics used to attach orthopedic prostheses, such as hip, knee, shoulder and other joint prostheses. CuNPs are incorporated into 4 mL of the liquid monomer/self-curing activator fraction in amounts of 0.79-6.28 mg, dispersed in ultrasound for 10 minutes and then mixed with bone acrylic powder in a ratio of 3:2 acrylic mass (grams):monomer volume (mL). Polymerisation is subsequently achieved under self-curing conditions.

The invention claimed is:

1. A dental and orthopedic material with antimicrobial properties comprising a polymethyl methacrylate (PMMA) matrix with randomly diffused or embedded metallic copper nanoparticles (CuNPs)) as sole active ingredient, wherein said nanoparticles have all their external dimensions between 40 and 100 nm and the CuNPs concentration in said material is between 0.045 wt. % and 0.053 wt. %; and wherein said metallic copper nanoparticles (CuNPs) contain copper having an oxidation number of 0 as their only copper component.

2. The dental and orthopedic material according to claim 1, wherein said material is selected from full denture prostheses, partial denture prostheses, removable denture prostheses, and permanently fixed denture prostheses.

3. The dental and orthopedic material according to claim 1, wherein said material exhibits antimicrobial activity against oral pathogens selected from *Candida albicans, Streptococcus mutans, Aggregatibacter actinomycetemcomitans* and *Staphylococcus aureus*.

4. A dental and orthopedic material with antimicrobial properties comprising a polymethyl methacrylate (PMMA) matrix with randomly diffused or embedded metallic copper nanoparticles (CuNPs) as sole active ingredient, wherein said nanoparticles have all their external dimensions between 40 and 100 nm and the CuNPs final concentration in said material is between 0.045 wt. % and 0.053 wt. %, wherein said metallic copper nanoparticles (CuNPs) contain copper having an oxidation number of 0 as their only copper component, and, wherein said material is formed by a method comprising:
(a) (i) adding 100 μL of an aqueous solution of copper acetate (Cu(CH3CQ0)2) of concentration 0.1 to 0.8 M to 95% ethanol, adding 2 mL of liquid methyl acrylate monomer (MMA) to the ethanolic solution under constant agitation and at room temperature, and constantly stirring the resulting solution between 50 to 70° C. until reddish-colored CuNPs are formed; or
(ii) alternatively, mixing an aqueous solution of copper acetate Cu(CH3CQ0)2) of concentration 0.1 to 0.8 M with particles of zeolite at a ratio of 0.5 g/100 mL, separating and purifying the zeolite by repeated centrifugation/dispersion cycles, and drying the CuNP/zeolite at 80° C. for two hours or by freeze-drying, and then dispersing the CuNP/zeolite in a 10% w/v starch/ascorbic acid reducing solution, microwaving the suspension for 60 seconds in 20-second intervals, and subsequently separating and washing the CuNPs/zeolite particles, and mixing the washed CuNPs/zeolite particles with 4 mL of liquid MMA and dispersing the mixture by sonication for 10 minutes; or
(iii) alternatively, mixing 0.79 to 6.28 mg of powdered CuNPs with 4 mL of liquid MMA and dispersing the mixture by sonication for 10 minutes;
(b) mixing the liquid monomer solution loaded with CuNPs obtained in step (a) with an amount of PMMA at a ratio acrylic/monomer of 3:2 (w/v);
(c) placing the mixture obtained in step (b) in polytetrafluoroethylene or dental muffle molds to complete the self- or thermo-curing process.

5. The dental and orthopedic material according to claim 4, wherein said material is selected from full denture prostheses, partial denture prostheses, removable denture prostheses, and permanently fixed denture prostheses.

6. The dental and orthopedic material according to claim 4, wherein said material exhibits antimicrobial activity against oral pathogens selected from *Candida albicans, Streptococcus mutans, Aggregatibacter actinomycetemcomitans* and *Staphylococcus aureus*.

7. A dental and orthopedic material with antimicrobial properties comprising a polymethyl methacrylate (PMMA) matrix with randomly diffused or embedded metallic copper nanoparticles (CuNPs) as sole active ingredient wherein said nanoparticles have all their external dimensions between 40 and 100 nm and the CuNPs final concentration in said material is between 0.045 wt. % and 0.053 wt. %; wherein said metallic copper nanoparticles (CuNPs) contain copper having an oxidation number of 0 as their only copper component, and, wherein said material is formed by a method comprising:
(a) (i) adding an aqueous solution of copper acetate (Cu(CH3CQ0)2) to ethanol, adding liquid methyl acrylate monomer (MMA) to the ethanolic solution, and maintaining the resulting solution between 50 to 70° C. until reddish-colored CuNPs are formed; or
(ii) alternatively, mixing an aqueous solution of copper acetate Cu(CH3CQ0)2) with particles of zeolite to form CuNP/zeolite particles, optionally purifying the particles, mixing the CuNPs/zeolite particles with liquid MMA and dispersing the mixture; or
(iii) alternatively, mixing powdered CuNPs with liquid MMA and dispersing the mixture;
(b) mixing the liquid monomer solution loaded with CuNPs obtained in step (a) with PMMA; and
(c) molding the mixture.

* * * * *